United States Patent
Meyre et al.

(10) Patent No.: US 11,278,723 B2
(45) Date of Patent: Mar. 22, 2022

(54) NANOPARTICLES FOR USE FOR TREATING A NEURONAL DISORDER

(71) Applicant: NANOBIOTIX S.A., Paris (FR)

(72) Inventors: Marie-Edith Meyre, Saint Mande (FR); Agnès Pottier, Paris (FR); Laurent Levy, Paris (FR)

(73) Assignee: NANOBIOTIX S.A., Paris (FR)

( * ) Notice: Subject to any disclaimer, the term of this patent is extended or adjusted under 35 U.S.C. 154(b) by 0 days.

(21) Appl. No.: 16/472,214

(22) PCT Filed: Dec. 19, 2017

(86) PCT No.: PCT/EP2017/083533
§ 371 (c)(1),
(2) Date: Jun. 21, 2019

(87) PCT Pub. No.: WO2018/114945
PCT Pub. Date: Jun. 28, 2018

(65) Prior Publication Data
US 2019/0351231 A1 Nov. 21, 2019

(30) Foreign Application Priority Data

Dec. 21, 2016 (EP) .................................... 16306750

(51) Int. Cl.
*A61P 25/00* (2006.01)
*A61N 1/36* (2006.01)
(Continued)

(52) U.S. Cl.
CPC ...... *A61N 1/36025* (2013.01); *A61K 41/0052* (2013.01); *A61N 2/006* (2013.01); *A61P 25/00* (2018.01); *B82Y 40/00* (2013.01)

(58) Field of Classification Search
CPC ..... A61N 1/36025; A61N 2/006; A61P 25/00; A61K 41/0052; B82Y 40/00
See application file for complete search history.

(56) References Cited

U.S. PATENT DOCUMENTS 10,588,987 B2    3/2020  Poul et al.
2011/0262347 A1* 10/2011 Ruoslahti ................ B82Y 5/00
                                                          424/1.11
(Continued)

FOREIGN PATENT DOCUMENTS

WO   WO 2006/126771    11/2006
WO   WO 2014/202723    12/2014
(Continued)

OTHER PUBLICATIONS

Guguru, R. et al. "Magnetoelectric 'spin' on stimulating the brain" *Nanomedicine*, 2015, pp. 2051-2061, vol. 10, No. 13.
(Continued)

*Primary Examiner* — Ankit D Tejani
*Assistant Examiner* — Joshua Brendon Solomon
(74) *Attorney, Agent, or Firm* — Saliwanchik, Lloyd & Eisenschenk

(57) ABSTRACT

The present invention relates to the medical field, in particular to the treatment of neurological disorders. More specifically the present invention relates to a nanoparticle or nanoparticles' aggregate for use in prevention or treatment of a neurological disease or at least one symptom thereof in a subject when the nanoparticle or nanoparticles' aggregate is exposed to an electric field, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100. It further relates to compositions and kits comprising such nanoparticles and/or nanoparticles' aggregates as well as to uses thereof.

9 Claims, 12 Drawing Sheets

Figure 1:
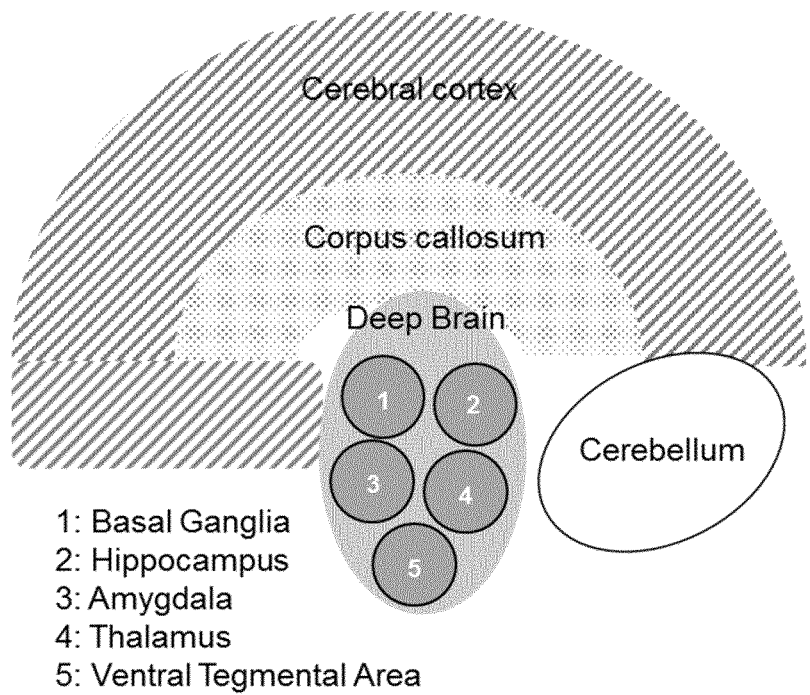

1: Basal Ganglia
2: Hippocampus
3: Amygdala
4: Thalamus
5: Ventral Tegmental Area

(51) Int. Cl.
*A61K 41/00* (2020.01)
*A61N 2/00* (2006.01)
*B82Y 40/00* (2011.01)

(56) References Cited

U.S. PATENT DOCUMENTS

| | | | |
|---|---|---|---|
| 2013/0204316 A1* | 8/2013 | Carpentier | A61B 8/0816 607/45 |
| 2013/0261683 A1* | 10/2013 | Soikum | C12N 13/00 607/2 |
| 2013/0317279 A1 | 11/2013 | Khizroev et al. | |
| 2013/0320273 A1 | 12/2013 | Kotov et al. | |
| 2014/0323946 A1* | 10/2014 | Bourke, Jr | A61N 5/062 604/20 |
| 2015/0202351 A1* | 7/2015 | Kaplan | A61L 31/10 607/116 |
| 2017/0000358 A1* | 1/2017 | Bae | G01K 7/16 |
| 2019/0351057 A1 | 11/2019 | Pottier et al. | |
| 2020/0086120 A1 | 3/2020 | Levy et al. | |

FOREIGN PATENT DOCUMENTS

| | | |
|---|---|---|
| WO | WO 2018/114988 | 6/2018 |
| WO | WO 2018/115023 | 6/2018 |

OTHER PUBLICATIONS

Written Opinion in International Application No. PCT/EP2017/083533, dated Apr. 16, 2018, pp. 1-7.
Borducchi, D. M. M. et al. "Transcranial Direct Current Stimulation Effects on Athletes' Cognitive Performance: An Exploratory Proof of Concept Trial" *Frontiers in Psychiatry*, Nov. 2016, pp. 1-5, vol. 7, Article 183.
Yong, J. et al. "Gold-Nanorod-Assisted Near-Infrared Stimulation of Primary Auditory Neurons" *Adv. Healthcare Mater.*, 2014, pp. 1862-1868, vol. 3, No. 11.
Paviolo, C. et al. "Laser exposure of gold nanorods can induce intracellular calcium transients" *J. Biophotonics.*, 2014, pp. 761-765, vol. 7, No. 10.
Shah, S. et al. "Hybrid upconversion nanomaterials for optogenetic neuronal control" *Nanoscale*, 2015, pp. 16571-16577, vol. 7, No. 40.
Chen, R. et al. "Wireless magnetothermal deep brain stimulation" *Science*, Mar. 12, 2015, pp. 1-7, vol. 347, No. 6229.
Ciofani, G. et al. "Enhancement of Neurite Outgrowth in Neuronal-Like Cells following Boron Nitride Nanotube-Mediated Stimulation" *ACS Nano*, 2010, pp. 6267-6277, vol. 4, No. 10.
Marino, A. et al. "Piezoelectric Nanoparticle-Assisted Wireless Neuronal Stimulation" *ACS Nano*, 2015, pp. 7678-7689, vol. 9, No. 7.
Written Opinion in International Application No. PCT/EP2017/083658, dated Mar. 16, 2018, pp. 1-10.
Written Opinion in International Application No. PCT/EP2017/083608, dated Mar. 15, 2018, pp. 1-8.
Claims as filed for U.S. Appl. No. 16/472,215, filed Jun. 21, 2019, pp. 1-3.
Claims as filed for U.S. Appl. No. 16/472,216, filed Jun. 21, 2019, pp. 1-4.
Park, J. S. et al. "Electrical Pulsed Stimulation of Surfaces Homogeneously Coated with Gold Nanoparticles to Induce Neurite Outgrowth of PC12 Cells" *Langmuir*, 2009, pp. 451-457, vol. 25.
Guduru, R. "Bionano Electronics: Magneto-Electric Nanoparticles for Drug Delivery, Brain Stimulation and Imaging Applications" *FIU Electronic Theses and Dissertations*, 2013, pp. 1-177, https://digitalcommons.fiu.edu/etd/979.
Polak, P. et al. "Nanometric agents in the service of neuroscience: Manipulation of neuronal growth and activity using nanoparticles" *Nanomedicine: Nanotechnology, Biology, and Medicine*, 2015, pp. 1467-1479, vol. 11.
Silva, L. H. A. et al. "Labeling mesenchymal cells with DMSA-coated gold and iron oxide nanoparticles: assessment of biocompatibility and potential applications" *J. Nanobiotechnol.*, 2016, pp. 1-15, vol. 14, No. 59.
Yue, K. et al. "Magneto-Electric Nano-Particles for Non-Invasive Brain Stimulation" *PLoS ONE*, Sep. 5, 2012, pp. 1-5, vol. 7, Issue 9, e44040.
Xia, X. et al. "Quantifying the Coverage Density of Poly(ethylene glycol) Chains on the Suface of Gold Nanostructues" *ACS Nano.*, Jan. 24, 2012, pp. 1-22, vol. 6, No. 1.

\* cited by examiner

NANOPARTICLES FOR USE FOR TREATING A NEURONAL DISORDER

CROSS-REFERENCE TO RELATED APPLICATION

This application is the U.S. national stage application of International Patent Application No. PCT/EP2017/083533, filed Dec. 19, 2017.

The present invention relates to the medical field, in particular to the treatment of neurological disorders. More specifically the present invention relates to a nanoparticle or nanoparticles' aggregate for use in prevention or treatment of a neurological disease or at least one symptom thereof in a subject when the nanoparticle or nanoparticles' aggregate is exposed to an electric field/stimulus, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100. It further relates to compositions and kits comprising such nanoparticles and/or nanoparticles' aggregates as well as to uses thereof.

BACKGROUND

Neurological disorders are a major health concern (*Neurological disorders public health challenges. WHO*, 2006). Impairment of neural network function may have different origins. Parkinson's disease is a movement disorder caused by death of dopamine neurons in the substantia nigra, located in the midbrain. Stroke corresponds to a block in the brain's blood supply. Without oxygen, neurons in the affected area die, and the part of the body controlled by those cells cannot function. Huntington's disease is a genetic disorder. Epilepsy is a disorder caused by abnormal excitation of large groups of neurons in various brain regions. Alzheimer's disease is a neurodegenerative disorder characterized by the death of neurons in the hippocampus, cerebral cortex, and other brain regions. The causes of autism spectrum disorders are multifactorial: genetic, environmental, etc.

Neurological disorders can be classified depending on the primary symptoms that affect the patients. Three main types of symptoms are observed: motor disorders, psychiatric (mood/social) disorders and cognitive disorders as further explained herein below.

Motor disorders encompass tremor, hypokinesia such as bradykinesia or dyskinesia, muscle twisting, rigidity, postural instability, gait freezing, etc. Diseases presenting motor disorders include typically Parkinson's disease, dystonia, epilepsy, Huntington's disease and Tourette's syndrome.

Psychiatric disorders constitute a variety of diseases presenting symptoms of mood/social impairments. A non-exhaustive list includes autism spectrum disorders, schizophrenia disorders, bipolar disorders, depressive disorders, anxiety disorders, obsessive-compulsive disorders, substance-related and/or addictive disorders (*definition from the Diagnostic and Statistical Manual of Mental Disorders*, 2013, fifth edition, the American Psychiatric Association). Some patients suffering of motor disorders, like Parkinson's disease and dystonia, can develop psychiatric disorders in the late stage of the diseases.

Cognitive disorders are present in many if not all mental disorders (e.g., schizophrenia, bipolar disorders). Only disorders whose core features are cognitive are included in the cognitive disorders category. Cognitive disorders affect the daily life of patients: simple tasks are complicated to achieve. Dementia is a representative cognitive disorder and it is a general term for a decline in mental ability severe enough to interfere with daily life. Alzheimer's disease is a peculiar type of dementia, with a neurodegenerative aspect.

Neurological disorders are, when possible, treated with drugs which play on regulation of the level of neurotransmitters in the brain and on control of interactions with their specific neurotransmitter receptors. The main neurotransmitters involved are: glutamate, γ-aminobutyric acid (GABA), dopamine and acetylcholine. Glutamate and GABA neurotransmitters are of peculiar interest because they play the principal role in increasing (Platt et al., *The Veterinary Journal*, 2007, 173, 278-286: *The role of glutamate in central nervous system health and disease—a review*) and in reducing neuronal excitability, respectively (Holmes et al., *Mental Retardation and Developmental Disabilities*, 1995, 1, 208-219: *Role of glutamate and GABA in the pathophysiology of epilepsy*). Dopamine is involved in several brain functions: control of movement via the basal ganglia (an improper level of dopamine in the basal ganglia results in uncontrolled movements), pleasure reward seeking behavior (disturbance may lead to dysfunctional addiction), cognition (disorders of dopamine in frontal lobes may lead to decline in neurocognitive functions), etc. (Alcaro et al., *Brain Res. Rev.*, 2007, 56(2), 283-321: *Behavioral functions of the mesolimbic dopaminergic system: an affective neuroethological perspective*). Acetylcholine is a neurotransmitter involved in learning and memory at the central nervous system level (Hasselmo et al., *Curr Opin Neurobiol*, 2006, 16(6), 710-715: *The role of acetylcholine in learning and memory*).

A common medication to alleviate the motor symptoms of Parkinson's disease is levodopa, which is transformed in dopamine in the brain and by this way helps in balancing the deficit in dopamine. Levodopa is associated to carbidopa, which helps in avoiding the levodopa transformation in dopamine in all the body. One issue of the levodopa treatment is the "on-off" phenomenon, which results in phases of immobility and incapacity associated with depression alternating with jubilant thaws (Lees et al., *J Neurology Neurosurgery Psychiatry, Special Supplement*, 1989, 29-37: *The on-off phenomenon*). Non-responsiveness of the late-stage Parkinson's disease patients to this treatment is an issue (Fabbri et al., *Parkinsonism and related disorders*, 2016: *Do patients with late-stage Parkinson's disease still respond to levodopa?*). Other common medications to treat symptoms of neuropsychiatric disorders, like the "positive" symptoms, delusions and hallucinations, in schizophrenia are antipsychotic drugs.

However, therapeutic treatments of neurological disorders' symptoms with drugs are non-specific, and as such, they may induce severe adverse events. In addition, refractoriness to the used drug may appear.

With advancing comprehension of neuroscience, brain can be thought as an electric network, coding and transmitting information through its electric wires, neurons. Connectivity between neurons is simple and complex at the same time: simple because it lies on influx/efflux of ions inside neurons, which result in action potentials (or "spikes" of electric activity); complex because the brain network is composed of hundreds of billion neurons, which form nodes, hubs and modules that demonstrate coordinated interactions, at various spatial and temporal scales (Fornito et al., *Nature Reviews Neuroscience*, 2015, 16, 159-172: *The connectomics of brain disorders*). Neural communication depends on the anatomical components that connect individual neurons (structure) and on the process of transmitting information (function). Both aspects affect the overall performance of the nervous system. Neuronal interactions are traduced by oscillations of the brain electric activity pattern, which oscillations are measurable typically by electroencephalogram (EEG). Different frequency bands of oscillations are observed: delta, theta, alpha, beta, gamma (Ward et al., *Trends in Cognitive Sciences*, 2003, 7(12), 553-559: *Synchronous neural oscillations and cognitive processes*). Structurally, the most striking neuroanatomical feature of the brain is the abundant connectivity between neurons, which reflects the importance of neural communication. Synchronization of oscillations ("synchrony") between one brain area and another seems to constitute the last level of information coding [first level (neuron): action potentials; second level (neuronal network(s)): neuronal oscillations] by bringing spatio-temporal coordination (Engel et al., *Nature Reviews Neuroscience*, 2001, 2, 704-716: *Dynamic predictions: oscillations and synchrony in top-down processing*). Importantly, evidence is emerging that a delicately balanced pattern of synchronization and desynchronization in space and time is fundamental to the functional performance of the nervous system (Schnitzler et al., *Nature Reviews Neuroscience*, 2005, 6, 285-296: *Normal and pathological oscillatory communication in the brain*). Abnormal synchronization processes (too high and/or too extended synchrony, i.e. also named hypersynchrony, or too low synchrony, i.e. also named impaired synchrony), have been associated with several brain disorders, such as epilepsy, schizophrenia, dementia and Parkinson's disease (Schnitzler et al., *Nature Reviews Neuroscience*, 2005, 6, 285-296: *Normal and pathological oscillatory communication in the brain*).

Nowadays, modulation of the electric activity pattern of neurons (neuromodulation) may be induced through electrical stimulations. The current techniques to produce an electric stimulus into the brain utilize either a direct electric stimulation or the induction of an electric field through the application of an electric current through a magnetic coil. Because certain neurological disorders affect areas in the deep brain and as the penetration depth of electric field is weak, the surgical implantation of electrodes inside the brain to continuously deliver electrical stimuli has been implemented and constitutes the "deep brain stimulation" (DBS) technique. Its efficacy depends on the parameters used for stimulation, especially the frequency. In 1987, high-frequency stimulation (≥100 Hz) of the ventralis intermedius (VIM) with implanted electrodes has been found to relieve the tremor symptoms for patients suffering from Parkinson's disease (Benabid et al., *Applied Neurophysiology*, 1987, 50, 344-346: *Combined (thalamotomy and stimulation) stereotactic surgery of the VIM thalamic nucleus for bilateral Parkinson disease*). Also, it has been shown in monkeys that high-frequency stimulation (>100 Hz), compared to low-frequency stimulation (<50 Hz), allows changes in the temporal firing pattern of neurons in the globus pallidus external (GPe) and the globus pallidus internal (GPi) (stimulus-synchronized regular firing pattern), which blocks transmission of altered patterns of neuronal activity in the basal ganglia to its target structures in the thalamus and the brainstem, thus alleviating the bradykinesia and rigidity symptoms (Hashimoto et al., *The Journal of Neuroscience*, 2003, 23(5), 1916-1923: *Stimulation of the subthalamic nucleus changes the firing pattern of pallidal neurons*). DBS is nowadays approved to treat several motor disorders (Parkinson's disease, dystonia, essential tremor, epilepsy) and psychiatric disorders (Obsessive Compulsive Disorder, depression).

However, several drawbacks may be associated to DBS, the first being the invasiveness of the technique and the risks of various complications like hemorrhage, epileptic seizures, infections, lead migration, lead breakage, etc. (Fenoy et al., *J Neurosurg*, 2014, 120, 132-139: *Risks of common complications in DBS surgery: management and avoidance*).

Focality (i.e. spatial resolution) of the generated electrical field in the target is another concern. The spread of electrical stimulus has also been linked to side-effects such as depression. A lot of research has been dedicated to design new types of electrodes which can shift and confine the stimulus within a certain area (Luan et al., *Frontiers in Neuroengineering*, 2014, 7(27), 1-9: *Neuromodulation: present and emerging methods*). Other technological aspects are under evaluation: the electrodes (or leads), their size, the invasiveness of the DBS device, the material constituting the leads, the compatibility with (magnetic resonance) imaging techniques, the battery life of the internal pulse generator (IPG) associated with the need for continuous stimulation.

The main others existing types of electrical stimulation, namely the transcranial electrical stimulation or transcranial magnetic stimulation, have the advantage not to be invasive, but the penetration depth of the electric field is weak. As such, their applications are limited to stimulation of the cerebral cortex (deep brain is not reachable). Moreover, the spatial resolution remains poor.

Electrical stimulation of brain remains a relevant method to treat neuronal disorders. However, there is a need for a more localized delivery of the electrical stimulus, and an increased depth of penetration without affecting the surrounding brain areas, to avoid side-effects such as psychiatric side-effects; ultimately increasing the treatment benefit/risk ratio.

Recently, non-invasive neural stimulation techniques have been envisaged, such as the use of light or ultrasound to directly stimulate neurons. Still, these techniques suffer from a poor spatial resolution. Interestingly, nanomaterials with unique properties have been explored as mediator to convert a wirelessly transmitted primary stimulus to a localized secondary stimulus, primarily electric field or heat, at the nanomaterial-neuron interface (Wang Y. & Guo L. *Frontiers in Neuroscience*. 2016; vol. 10, Article 69, *Nanomaterial-enabled neural stimulation*). Thus, opto-electric transduction has been shown using quantum dots, opto-thermal transduction using gold nanomaterials, magneto-electric transduction using magneto-electric nanoparticles, magneto-thermal transduction using superparamagnetic nanoparticles and acousto-electric transduction using piezo-electric nanomaterials.

Most of these emerging techniques using nanomaterials require the concurrent development of the energy source to provide neural stimulation. Moreover, the incoming energy needs to be transduced into an efficient secondary stimulus which requires well-defined nanoparticle's structure and composition as well as persistence of the nanoparticle's structure and composition overtime.

For instance, magneto-electric (ME) nanoparticles are composite nanoparticles exhibiting piezoelectric and magnetostrictive properties. Concretely, the ME effect allowed for example by $CoFe_2O_4$—$BaTiO_3$ nanoparticles results from the combined actions of two distinct materials, i.e. a magnetostrictive ($CoFe_2O_4$) material and a piezoelectric ($BaTiO_3$) material. More precisely, when $CoFe_2O_4$—Ba- TiO₃ nanoparticles are exposed to a magnetic field: first, the magnetostrictive material changes its length (volume), thereby causing a local stress, second, the piezoelectric material produces an electric polarization (a charge) as a reaction to this local stress. None of the magnetostrictive material or of the piezoelectric material is capable of generating by itself either a ME effect or an electric polarization when exposed to a magnetic field, as explained by Grössinger R. et al. (Grössinger R. et al., *Journal of Magnetism and Magnetic Materials*, 2008, 320, 1972-1977: *The physics of magnetoelectric composites*).

The present invention deals with nanoparticles and/or nanoparticles' aggregates (aggregates of nanoparticles) for use for preventing or treating/for use in prevention or treatment of a neurological disease (typically neuronal networks' disorders) or at least one symptom thereof, when the nanoparticle or nanoparticles' aggregate is exposed to an electric field. The electric field is typically applied through deep brain stimulation (DBS), transcranial electric stimulation (TES) or transcranial magnetic stimulation (TMS).

The nanoparticles or nanoparticles' aggregates normalize the synchronization of neuronal oscillations (improve synchrony) within and/or between neuronal networks, and within and/or between distinct regions of the brain, and enhance the spatial resolution (focality) of the electrical stimulation, while using standard electrical stimulation techniques. Nanoparticles or nanoparticles' aggregates herein described by inventors thus help the subject/patient to return to a healthy state.

Moreover, the nanoparticles or aggregates of nanoparticles of the present invention allow a decrease of the applied current, voltage, pulse width and/or frequency and therefore reduce the known potential toxicity related to the applied/induced electrical current.

BRIEF DESCRIPTION

Herein advantageously described for the first time is a nanoparticle or nanoparticles' aggregate for use for preventing or treating/for use in prevention or treatment of a neurological disease or at least one symptom thereof in a subject in need thereof when the nanoparticle or nanoparticles' aggregate is exposed to/excited or activated by an electric field/stimulus. The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Also herein described is the use of a nanoparticle or nanoparticles' aggregate for preparing a composition for preventing or treating a neurological disease as herein described or at least one symptom thereof in a subject in need thereof.

Also herein described is a composition for use for preventing or treating/for use in prevention or treatment of a neurological disease or at least one symptom thereof in a subject exposed to an electric field, wherein the composition comprises, or consists of, nanoparticles and/or nanoparticles' aggregates and a pharmaceutically acceptable support, and wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Further herein described is a kit comprising at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100, and uses thereof typically in prevention or treatment of/in a method for preventing or treating a neurological disease or at least one symptom thereof in a subject.

DETAILED DESCRIPTION

The human nervous system is estimated to consist of roughly 80-120 billion nerve cells (Herculano-Houzel S. *Frontier in Human Neuroscience* (2009), 3(31): 1-11, *The human brain in numbers: a linearly scaled-up primate brain*). The defining characteristic of a neuron (or nerve cell) is its ability to transmit electrical signals in the form of action potentials.

The neuron/nerve cell constitutes the elementary node of the brain. Nerve cells can communicate with each other in a highly-structured manner forming neuronal networks. Neuron communicates via synaptic connections. Within neuron, nanocircuits constitute the underlying biochemical machinery for mediating key neuronal properties such as learning and memory and the genesis of neuronal rhythmicity.

A microcircuit can be formed with just only a few interconnected neurons and can perform sophisticated tasks such as mediate reflexes, process sensory information, initiation of locomotion, and learning and memory mediation. A macrocircuit is a more complex network which consists of multiple imbedded microcircuits. Macrocircuits mediate higher brain functions such as object recognition and cognition. So, multiple levels of networks occupy the nervous system.

Neural Network Excitability

Neurons send messages electrochemically (i.e. chemicals/ions cause an electrical signal). The important ions in the nervous system are sodium and potassium, calcium and chloride. When a neuron is not sending a signal, it is "at rest." When a neuron is at rest, the inside of the neuron is negative relative to the outside. Although the concentrations of the different ions attempt to balance out on both sides of the membrane, they cannot because the cell membrane allows only some ions to pass through channels (ion channels). In addition to these selective ion channels, there is a pump that uses energy to move three sodium ions out of the neuron for every two potassium ions it puts in. Finally, when all these forces balance out, and the difference in the voltage between the inside and outside of the neuron is measured, the resting membrane potential (also "resting potential") of a neuron is about −70 mV. This means that the inside of the neuron is 70 mV less than the outside. At rest, there are relatively more sodium ions outside the neuron and more potassium ions inside that neuron. An action potential (also identified as "spike" or "impulse") occurs when a neuron sends information down an axon, away from the cell body. This means that some event (a stimulus) causes the resting potential to move toward 0 mV. When the depolarization reaches about −55 mV the neuron fires an action potential. If the depolarization does not reach this critical threshold level, then no action potential fires (on/off mechanism). Also, when the threshold level is reached, an action potential of fixed amplitude always fires. Therefore, either the depolarization does not reach the threshold or a full action potential is generated.

A great variability is found in the velocity of the propagation of action potentials. In fact, the propagation velocity of the action potentials in nerves can vary from 100 meters per second to less than a tenth of a meter per second. Whereas the time constant is an index of how rapidly a membrane will respond to a stimulus in time, the space constant (also length constant) is an index of how well an electric potential will spread along an axon as a function of distance.

Connectivity Within and Between Neuronal Networks

There are three connectivity network types that are used to investigate communication within and across the brain. Structural connectivity is based on the detection of the fiber tracks that physically connect the regions of the brain. These are the anatomical network maps that indicate possible pathways that the signals can travel on in the brain. Functional connectivity identifies activity in brain regions that have similar frequency, phase and/or amplitude of correlated activity. Effective connectivity uses the functional connectivity information and goes one step further and determines the direct or indirect influence that one neural system may have over another, more specifically the direction of the dynamic information flow in the brain (Bowyer et al., *Neuropsychiatric Electrophysiology*, 2016, 2(1), 1-12: *Coherence a measure of the brain networks: past and present*).

The synchronized activity within a neuronal network can be detected by magnetoencephalogram (MEG), electroencephalogram (EEG), Functional Magnetic Resonance Imaging (FMRI) or Positron Emission Tomography (PET), then image using network connectivity analysis. MEG (Magnetoencephalogram) or EEG (Electroencephalogram) are preferred because they have high temporal resolution to resolve the dynamic flow of information. Connectivity analysis of the brain is performed to map out the communication networks needed for the brain to function. Specific regions in the brain are specialized for processing certain types of information. Imaging techniques have revealed that these regions are connected and communicate with other specialized regions across networks in the brain. "Coherence" (Bowyer et al., *Neuropsychiatric Electrophysiology*, 2016, 2(1), 1-12: *Coherence a measure of the brain networks: past and present.*) is a mathematical technique that quantifies the frequency and amplitude of the synchronicity (the state of being in synchrony or of being synchronized) of neuronal patterns of oscillating brain activity. Detection of the synchronous activation of neurons can be used to determine the wellbeing or integrity of the functional connectivity in the human brain. Overlaying the functional connectivity maps onto the structural connectivity images and the using direction of information flow derived from effective connectivity provides an all-inclusive understanding of how the brain functions. These techniques help to evaluate treatment therapies based on pre- and post-treatment brain connectivity imaging.

The intact brain expresses complex patterns of synchronous activity, associated with different 'states' of the organism, from slow delta rhythm (0.5-4 Hz), through theta (4-8 Hz), alpha (8-12 Hz), beta (15-30 Hz) and gamma (30-70 Hz) oscillations. Interestingly, the dissociated culture of cortical structures offers a convenient system for the examination of the rules that govern the emergence, generation and spread of network firing (spikes) and bursting (clusters of spikes) in populations of densely interconnected neurons. Network activity can be recorded for extended periods of time in a non-invasive manner and with finite time resolution using multielectrodes arrays. The 2-dimensional dissociated culture can be used as a viable test system for studying rules that govern the formation and maintenance of network activity in the brain, allowing the testing of hypothesis that cannot be addressed in the intact brain (Cohen E. et al., *Brain Research*, 2008, 1235, 21-30: *Determinants of spontaneous activity in networks of cultured hippocampus*).

Herein advantageously described for the first time is a nanoparticle or nanoparticles' aggregate for use for preventing or treating/for use in prevention or treatment of a neurological disease or at least one symptom thereof in a subject in need thereof when the nanoparticle or nanoparticles' aggregate is exposed to an electric field. The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

The term "Treatment" refers to therapeutic treatment or measures able to prevent, alleviate or cure a disease, disorder or dysfunctional state as herein described. Such a treatment is intended for a mammal subject, preferably a human subject in need thereof. Are considered as such, the subjects already identified (diagnosed) as suffering from a disease, disorder or dysfunctional state as herein described, or those considered "at risk of developing" such a disease, disorder or dysfunctional state for whom the treatment is a preventive or prophylactic treatment.

Abnormal modulation of the oscillatory communication between neurons indeed exists in different types of neurological diseases or disorders (also herein identified as "neural diseases or disorders") (Uhlhaas et al., *Neuron*, 2006, 52, 155-168: *Neural synchrony in brain disorders: relevance for cognitive dysfunctions and pathophysiology*; Basar E. et al. *International Journal of Psychophysiology* 103 (2016) 135-148, *What does the broken brain say to the neuroscientist? Oscillations and connectivity in schizophrenia, Alzheimer's disease, and bipolar disorder*).

The human nervous system is divided into the central nervous system (CNS) and the peripheral nervous system (PNS). The CNS, in turn, is divided into the brain and the spinal cord, which lie in the cranial cavity of the skull and the vertebral canal, respectively. The CNS and the PNS, acting in concert, integrate sensory information and control motor and cognitive functions. FIG. 1 shows a simplified picture of the brain structure.

Synchrony (or synchronization) within and/or between neuronal networks, within and/or between distinct regions of the brain, is performed through the coordination of neuronal oscillations in time (Buzsaki et al., *Science*, 2004, 304, 1926-1929: *Neuronal oscillations in cortical networks*). Motor disorders are typically due to hypersynchrony, which means that synchronization of oscillations within and/or between neuronal networks within and/or between distinct regions of the brain is too high and/or too extended. Psychiatric and cognitive disorders are typically due to an impaired synchrony, which means that synchronization of oscillations within and/or between neuronal networks within and/or between distinct regions of the brain is lowered (typically presents a reduced activity) or even disappears (cf. Table 1: Abnormal neural synchrony in neurological disorders (adapted from Uhlhaas et al., *Neuron*, 2006, 52, 155-168: *Neural synchrony in brain disorders: relevance for cognitive dysfunctions and pathophysiology*).

TABLE 1

| Type of symptoms | Neurological disorder | Neural synchrony |
|---|---|---|
| Motor | Parkinson's disease | high |
| | Epilepsy | |
| | Dystonia | |
| Psychiatric | Schizophrenia | impaired |
| | Autism | |
| Cognitive | Alzheimer's disease | |

Figure 2:
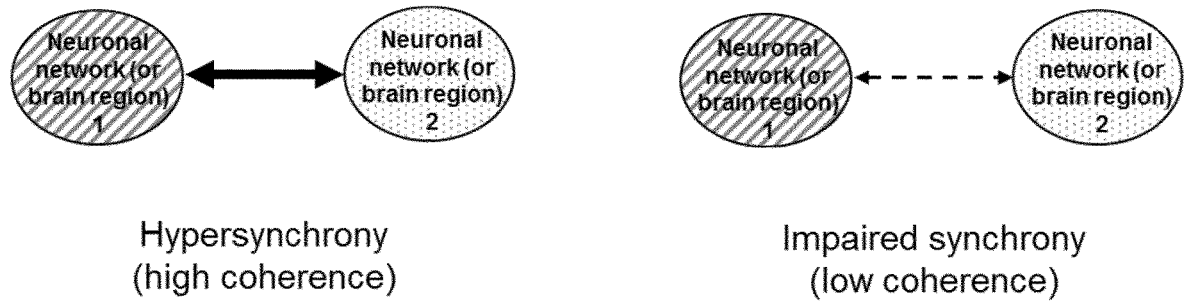

As "coherence" is a mathematical technique that quantifies the frequency and amplitude of the synchronicity (the state of being in synchrony or of being synchronized) of neuronal patterns of oscillating brain activity, it can be thought that a too high and a too low coherence are involved in motor disorders and psychiatric/cognitive disorders, respectively (Bowyer et al., *Neuropsychiatric Electrophysiology*, 2016, 2(1), 1-12: *Coherence a measure of the brain networks: past and present*) (cf. FIG. 2).

In a particular aspect, the neurological disease or disorder targeted in the context of the invention is selected from Parkinson's disease, Alzheimer's disease, epilepsy, obsessive compulsive disorder, autism spectrum disorder, depression disorder, dystonia, Tourette's syndrome, schizophrenia, stroke, aphasia, dementia, tinnitus, Huntington's disease, essential tremor, bipolar disorder, anxiety disorder, addiction disorder, consciousness vegetative state, for example selected from Parkinson's disease, Alzheimer's disease, epilepsy, obsessive compulsive disorder, autism spectrum disorder, depression disorder, dystonia, Tourette's syndrome, schizophrenia, stroke, aphasia, dementia, tinnitus, Huntington's disease, essential tremor, bipolar disorder, addiction disorder, consciousness vegetative state, and at least one symptom thereof.

As already explained herein above, neurological diseases or disorders can be classified depending on the primary symptoms that affect the patients which are motor disorders, psychiatric (mood/social) disorders and cognitive disorders as further detailed herein below.

Example of Motor Disorders

Parkinson's Disease

Parkinson's disease (PD) affects about 7 to 10 million people worldwide and it is characterized by tremor, dyskinesia, bradykinesia, gait freezing, etc. PD is a slowly progressive, degenerative disease of the brain. It affects nerve cells in the areas of the brain called the basal ganglia and the substantia nigra. Nerve cells in the substantia nigra produce dopamine, a neurotransmitter that acts as a chemical messenger in brain circuits important for planning and controlling body movement. In PD, the dopamine producing nerve cells of the substantia nigra die off prematurely in some individuals (Corti et al., *Physiol Rev*, 2011, 91, 1161-1218: *What genetics tells us about the causes and mechanisms of Parkinson's disease*). When dopamine receptors in the striatum are not adequately stimulated, parts of the basal ganglia are either under- or over-stimulated. In particular, the subthalamic nucleus (STN) becomes overactive and acts as an accelerator on the globus pallidus internus (GPi). The over-stimulation of the GPi has an over-inhibitory effect on the thalamus, which in turn decreases its output and causes slowing of motion, and rigidity (Guo et al., *Frontiers in Computational Neuroscience*, 2013, 7, 124, 1-11: *Basal ganglia modulation of thalamocortical relay in Parkinson's disease and dystonia*).

The lack of dopamine in PD has been related to excessive oscillatory synchronization in the beta frequency throughout the cortical-basal ganglia motor network. Indeed, the dopamine levels in the basal ganglia are predicted to suppress beta synchrony, which in turn mediate the dopaminergic involvement necessary for movement anticipation (Jenkinson et al., *Trends in Neuroscience*, 2011, 34(12), 611-618: *New insights into the relationship between dopamine, beta oscillations and motor function*). If the level of dopamine in the basal ganglia is not high enough, then there is no control of beta oscillations synchrony anymore, and slowness of movements may appear. Another observation in parkinsonian patients leads to the conclusion that cortical oscillations in the beta band, lead and drive those in the basal ganglia (Lalo et al., *The Journal of Neuroscience*, 2008, 28(12), 3008-3016: *Patterns of bidirectional communication between cortex and basal ganglia during movement in patients with Parkinson disease*).

Deep Brain Stimulation (DBS) can be used to treat the symptoms of tremor and rigidity (Eusebio et al., *J Neurol Neurosurg Psychiatry*, 2011, 82, 569-573: *Deep brain stimulation can suppress pathological synchronization in parkinsonian patients*). The treatment of PD symptoms by DBS is FDA-approved since 2002 (essential tremor since 1997). The most commonly used stimulatory parameters, usable in the context of the invention in combination with the herein described nanoparticles, are: 130 to 185 Hz in frequency, 60 to 210 µs in pulse width and 1 to 3.5 V in voltage amplitude (Kuncel et al., *Clinical Neurophysiology*, 2004, 115, 2431-2441: *Selection of stimulus parameters for DBS*). The electrical stimulation is typically performed in basal ganglia, in the STN and in the GPi. As mentioned above, cortical beta-oscillations are also involved in the pathophysiology of the disease, so transcranial stimulation (such as transcranial magnetic stimulation—TMS) of the cortex could also be used to treat the Parkinson's disease symptoms (Cantello et al., *Brain Research Reviews*, 2002, 38, 309-327: *Transcranial magnetic stimulation and Parkinson's disease*).

Dystonia

Dystonia is a neurological disorder characterized by abnormal, involuntary twisting and turning movements that reflect impaired motor system function. Several forms of dystonia exist, depending on the part of the body affected by the symptoms, on their genetic origin, on the type of neurotransmitter involved, etc. The dystonic Central Nervous System (CNS) exhibits a deficient inhibition, which provokes the loss of reciprocal spinal inhibition between opposing muscles. In the case of upper dystonia for example, an abnormal synchronization of neurons/nerves giving the input signal to the forearm antagonist muscles leads to co-contraction of these antagonist muscles (dystonic symptom) (Farmer et al., *Brain*, 1998, 121, 801-814: *Abnormal motor unit synchronization of antagonist muscles underlies pathological co-contraction in upper limb dystonia*).

The DBS target point showing interesting antidystonic effect is the globus pallidus internus (GPi-DBS). GPi-DBS was approved by FDA in 2003 for patients with chronic, medically intractable dystonia (Hu et al., *Translational Neurodegeneration*, 2014, 3(2), 1-5: *Deep brain stimulation for dystonia*). Stimulation of the ventral intermediate (VIM) nucleus of the thalamus (VIM-DBS) produces much less robust effects. Stimulation using the subthalamic nucleus (STN-DBS) has been experimental. GPi-DBS provides relief of the main symptoms of dystonia, but it can take weeks to months for the therapeutic effects to fully develop (Dressler et al., *J Neural Transm*, 2015, DOI 10.1007/s00702-015-1453-x: *Strategies for treatment of dystonia*). The most commonly used stimulatory parameters, usable in the context of the invention in combination with the herein described nanoparticles, are: frequency 130-180 Hz; pulse width 60-210 µs; amplitude 2-5 volts.

Epilepsy

Epilepsy is a brain disorder, which affects about 50 million people worldwide, and which is characterized predominantly by recurrent and unpredictable interruptions of normal brain function, called epileptic seizures. Epilepsy is not a singular disease entity but a variety of disorders reflecting underlying brain dysfunction that may result from many different causes (genetic mutation, brain tumors, head trauma, strokes, alcoholism, inflammation of the brain, infections such as meningitis, HIV or viral encephalitis, etc.) (Fisher et al., *Neurology,* 2015, 28(2), 130-135: *Redefining epilepsy*).

An epileptic seizure is defined as a transient occurrence of signs and/or symptoms due to excessive synchronous neuronal activity in the brain (Fisher et al., *Epilepsia,* 2005, 46(4), 470-472: *Epileptic seizures and epilepsy: definitions proposed by the International League Against Epilepsy (ILAE) and the International Bureau for Epilepsy (IBE)*). Cerebral cortex is the primary element in the generation of epileptic seizures: many people are diagnosed with focal frontal lobe or medial temporal lobe seizures (*National Institute of Neurological Disorders and Stroke*: Worldwide Website: ninds.nih.gov/disorders/epilepsy/detail epilepsy.htm#3109_7). The identification of areas of elevated local synchrony, or "hypersynchrony", in the cortex suggests that local hypersynchrony may be a marker of seizure-generating areas (Schevon et al., *Neuroimage,* 2007, 35(1), 140-148: *Cortical abnormalities in epilepsy revealed by local EEG synchrony*).

Neurostimulation for treatment of epilepsy can take the form of peripheral nerve stimulation, such as vagus nerve stimulation (VNS); spinal cord stimulation; transcranial brain stimulation (TES or TMS); or deep brain stimulation (DBS). Responsive neurostimulation is another strategy, where stimulation is delivered only when seizure onset is detected. In 2004, a proof-of-principle study of responsive neurostimulation in three patients with epilepsy was published, in which two patients were treated via cortical grid or strip electrodes, and one via hippocampal depth electrodes. Individual seizures could be truncated at the onset of stimulation, and overall seizure frequency was reduced by 50-75% (Kossoff et al., *Epilepsia,* 2004, 45, 1560-1567: *Effect of an external responsive neurostimulator on seizures and electromagnetic discharges during subdural electrode monitoring*). VNS and responsive neurostimulation have both been approved by the FDA for the treatment of certain types of epilepsy in the USA. DBS of the anterior nucleus of the thalamus (ANT) has been approved in countries of the European Union (Fisher et al., *Nature Reviews Neurology,* 2014, 10, 261-270: *Electrical brain stimulation for epilepsy*). A multicenter randomized controlled trial of bilateral stimulation of the anterior nucleus of the thalamus for epilepsy (SANTE) was performed in 110 adult patients who had partial seizures with or without secondary generalization at least six times per month, but not more than 10 times per day. Baseline seizure frequency was recorded for 3 months, followed by DBS lead implantation, 1 month of recovery, and then a 3-month blinded period of either active stimulation or no stimulation (placebo). On-stimulation parameters were 1 min of 90 µs pulses of 5V at 145 Hz followed by 5 min without stimulation. Seizure frequency decreased from baseline by a median of 20% during the 1-month recovery period. Thereafter, seizure frequencies in the two treatment groups significantly diverged, with a median improvement of 40.4% in the active group and 14.5% in the placebo group. The active group experienced significantly fewer complex partial seizures, and significantly fewer seizures of the type prospectively designated as "most severe" by the patients (Fisher et al., *Epilepsia,* 2010, 51, 899-908: *Electrical stimulation of the anterior nucleus of thalamus for treatment of refractory epilepsy*). Herein described conditions of electric stimulation/treatment can be used in the context of the invention in combination with the herein described nanoparticles.

Examples of Psychiatric Disorders (Mood/Social Impairments)

Obsessive Compulsive Disorders (OCD)

Obsessive-compulsive disorder (OCD) is a common psychiatric disorder that is often chronic, severe, and extremely debilitating. It is also usually refractory to treatments, with a substantial proportion of patients failing to respond or obtaining only partial relief.

Functional neuroimaging studies have demonstrated dysfunction in the orbitofrontal cortex, basal ganglia and striatum.

A study has shown that acute OCD symptoms may be related to an abnormal high oscillatory activity in the subthalamic nucleus (STN), particularly in the left hemisphere and in the delta-alpha (1-12 Hz) frequency range (Bastin et al., *Cortex,* 2014, 60, 145-150: *Changes of oscillatory activity in the subthalamic nucleus during obsessive-compulsive disorder symptoms: two case reports*). Furthermore, some subthalamic neurons specifically increased their firing rate when doubt occurred during a verification task (Burbaud et al., *brain,* 2013, 136(1), 304-317: *Neuronal activity correlated with checking behavior in the subthalamic nucleus of patients with obsessive-compulsive disorder*).

DBS of the ventral anterior limb of the internal capsule (VC) and adjacent ventral striatum (VS) was approved in the EU for the treatment of severe and highly resistant-treatment OCD (VC/VS-DBS). To demonstrate the therapeutic promise of the procedure, four clinical centers have collaborated most closely, in small-scale studies, over 8 years, and their data were analyzed (Greenberg et al., *Molecular Psychiatry,* 2010, 15, 64-79: *Deep brain stimulation of the ventral internal capsule/ventral striatum for obsessive-compulsive disorder: worldwide experience*). DBS leads were implanted bilaterally to stimulate the dorsal-ventral extent of the anterior capsule. The electrical stimulus frequency was at 100-130 Hz, at pulse widths ranging from 90 to a maximum of 450 µs. DBS intensities generally ranged from 2 to 8 V, resulting in currents ranging approximately from 2 to 15 mA, depending on electrode impedance (generally 500-1000Ω). In conclusion of these combined data, clinically significant symptom reductions and functional improvements were seen in about two-thirds of highly treatment-resistant patients (total of 26 patients), indicating encouraging therapeutic effects after VC/VS-DBS. Herein described conditions of electric stimulation/treatment can be used in the context of the invention in combination with the herein described nanoparticles.

Autism Spectrum Disorders

Autism is a neurodevelopmental syndrome that is defined by deficits in social reciprocity and communication, and by unusual restricted, repetitive behaviors. Autism is a disorder that usually begins in infancy, at the latest, in the first three years of life. Autism is a heterogeneous condition (no two children or adults with autism have similar profile), which has led to the concept of "autism spectrum disorder", classifying several levels of the disease according to the degree of language deficit or general cognitive delay, and according to the severity of social or behavioral symptoms (Lord et al., *Neuron,* 2000, 28, 355-363: *Autism spectrum disorders*). At one end of this spectrum, individuals with autism are high functioning, enabling them to live on their own and maintain employment. Individuals characterized as low functioning exhibit more severe symptoms: difficulties for language (or even nonverbal language), poor social communication, self-injurious behavior (SIB), tantrums, and aggression that can be potentially life threatening. An important trend in structural and functional studies of the brain in autism is the involvement of the network for socioemotional processing: the limbic system, the facial processing system and the mirror neuron network. A deficit in synchronization of gamma-band oscillations has been shown to be involved in the apparition of symptoms (Sinha et al., *Neurosurgery Focus,* 2015, 38(6), *E*3: *Deep brain stimulation for severe autism: from pathophysiology to procedure*).

Two major symptom domains that may require treatment in severe autism are social deficits, including being nonverbal and nonresponsive to speech, and SIB, which can be life threatening. The amygdala seems to play an important role in the pathophysiology of these abnormalities. Altered excitatory or inhibitory control is implicated in the abnormality of autism pathophysiology. Neuromodulation of amygdalar targets via DBS may represent a therapeutic intervention for patients with severe autism. Three cases of DBS treatment were reported in literature. The aim of treatments was mainly to alleviate motor disorders like the stereotypies (repeated movement pattern) and the self-injurious behaviors (SIB) associated to the disease (Sinha et al., *Neurosurgery Focus,* 2015, 38(6), *E*3: *Deep brain stimulation for severe autism: from pathophysiology to procedure*; Stocco et al., *Parkinsonism and related disorders,* 2014, 20, 1035-1036: *Deep brain stimulation for severe secondary stereotypies*). The DBS parameters, which can be used in the context of the invention in combination with the herein described nanoparticles, are: 80 to 130 Hz in frequency, 120 to 210 µs in pulse width, and 2.5 to 6.5 V in voltage amplitude (Sinha et al., *Neurosurgery Focus,* 2015, 38(6), *E*3: *Deep brain stimulation for severe autism: from pathophysiology to procedure*). In one of the three cases, it was reported that DBS in the basolateral nucleus resulted in a significant improvement in autism-related symptoms like social contact, affect modulation and nocturnal sleep (Sturm et al., *Frontiers in Human Neuroscience,* 2013, 6, 341, 1-10).

Schizophrenia

Schizophrenia is a chronic psychiatric illness characterized among others by the following symptoms: positive symptoms, which reflect aberrant mental activity (hallucinations and delusions); negative symptoms, which correspond to the deficiency of a mental function which is normally present (thought disorder, blunting of affect, poverty of speech). Regarding the causes of disability in the lifespan, schizophrenia is located within the top ten.

Prominent ventricular enlargement and increased cerebrospinal fluid on the brain surface suggest that the brain has atrophied. This loss of gray matter and the reduced numbers of synaptic structures on neurons suggest that schizophrenia is a neurodevelopmental disorder, which means that brain abnormalities are already present in first-episode patients (in contrast to neurodegenerative disorder).

In schizophrenia patients, the observed impaired neural circuitry has been demonstrated to be due to a failure of gamma-band synchronization (Spencer et al., *The Journal of Neuroscience,* 2003, 23(19), 7407-7411: *Abnormal neural synchrony in schizophrenia*; Gallinat et al., *Clinical Neurophysiology,* 2004, 115, 1863-1874: *Reduced oscillatory gamma-band responses in unmedicated schizophrenic patients indicate impaired frontal network processing*).

Electroconvulsive therapy (ECT), i.e. shock treatment, has been demonstrated to be one of the most successful non-pharmacological treatments in schizophrenia (Payne et al., *J. Psychiatr. Pract.,* 2009, 15(5), 346-368: *Electroconvulsive therapy part I: a perspective on the evolution and current practice of ECT*) and is herein usable in the context of the invention in combination with the herein described nanoparticles. It involves the successive application of electrical current to the brain, which provokes seizures comparable to epileptic ones.

Electric stimulation for the symptomatic treatment of schizophrenia is also possible through DBS. For example, DBS (145 Hz in frequency, 90 µs in pulse width, 4V in voltage amplitude) of the nucleus accumbens (NAcc) in depression leads to remission of anhedonia, i.e. recovery of hedonic pleasure (Schlaepfer et al., *Neuropsychopharmacology,* 2008, 33, 368-377: *Deep brain stimulation to reward circuitry alleviates anhedonia in refractory major depression*) and is usable in the context of the invention in combination with the herein described nanoparticles.

Example of Cognitive Disorder

Alzheimer's Disease

Alzheimer's disease (AD) is a neurodegenerative disorder and it leads to progressive loss of mental, behavioral, functional decline and ability to learn. Approximately 200 000 people younger than 65 years with AD comprise the younger onset AD population; 5 million are age 65 years or older.

Recent evidence indicates that cognitive deficits seen in Alzheimer's disease are associated with a functional disconnection of neuro-cognitive networks. Analyses of global EEG synchronization reveal a widespread reduction in the alpha-, beta- and gamma-band synchronization, concomitant with an increase in the delta-band synchronization. In patients with mild Alzheimer's disease, a loss of beta-band synchronization has been shown to correlate with cognitive impairment (Schnitzler et al., *Nature Reviews Neuroscience,* 2005, 6, 285-296: *Normal and pathological oscillatory communication in the brain*). Clinical investigations are ongoing to evaluate the potential of DBS for the treatment of Alzheimer's disease. The stimulatory parameters, typically usable in the context of the invention in combination with the herein described nanoparticles, are: 130 Hz in frequency, 60 or 90 µs in pulse width, 3 to 5 V in amplitude voltage (Laxton et al., *World Neurosurgery,* 2013, 80, S28.E1-S28.E8: *Deep brain stimulation for the treatment of Alzheimer disease and dementias*).

Electrical Stimulation

In the context of the invention, the electric field is preferably applied through deep brain stimulation, transcranial electric stimulation or transcranial magnetic stimulation. The vagus nerve stimulation (VNS) and spinal cord stimulation can also be applied in the context of the invention, such as in the context epilepsy. Any other known distinct electrical stimulation method can be used in the context of the invention such as the method described in Grossman N. et al. (*Cell,* 2017, 169, 1029-1041: *Noninvasive deep brain stimulation via temporally interfering electric fields*) which is a non-invasive deep brain stimulation carried out via temporally interfering electric fields.

In the context of the invention, the two main brain areas for electrical stimulation are the deep brain and the cerebral cortex.

The electrical stimulation can reach the deep brain, thanks to the surgical implantation of an electrode [penetration depth of the electrodes under the skin surface is to be equal to or above 10 cm and the penetration range of the electric field generated by the electrodes is of a few millimeters.: Deep Brain Stimulation (DBS)].

When the cerebral cortex is to be reached, the electrical stimulation is performed on the surface (penetration depth of the electric field is usually equal to or below 2 cm under the skin surface; with specific technique—specific coils for Transcranial Magnetic Stimulation—the electric field can reach 5 cm depth). Techniques providing such an electric field include typically Transcranial Magnetic Stimulation (TMS), repetitive Transcranial Magnetic Stimulation (rTMS), transcranial Direct Current Stimulation (tDCS), High-definition transcranial Direct Current Stimulation (HD-tDCS), Transcranial Electrical Stimulation (TES), transcranial Alternating Current Stimulation (tACS), transcranial Pulsed Current Stimulation (tPCS) and transcranial Random Noise Stimulation (tRNS; alternate current along with random amplitude and frequency). The most widely used in clinical trials, and preferred in the context of the invention, are TMS and tDCS.

Deep Brain Stimulation

The DBS device comprises three key components: a stimulating electrode (also called a lead), an extension cable, and a programmable pulse generator (PG), which resembles a cardiac pacemaker. The device is implanted in two stages. During the first stage uni- or bilateral-lead(s) are implanted stereotactically into a specific therapeutic target in the deep brain. During the second stage, which may be performed on the same day or later, the pulse generator(s) is(are) implanted under the skin of the anterior chest wall (below clavicle) or the abdomen, and connected to the lead wire(s) via subcutaneously tunneled extension cables. The lead is generally 40 cm in length and 1.27 mm in diameter, and it presents multiple contact electrodes (most of the time 4 contact electrodes on the lead—i.e. quadripolar electrode) of 1.5 mm or 3 mm in width depending on the indication, and spaced by 0.5 to 4 mm on the lead. One or two contact electrodes can be stimulated (when two electrodes are used, one is the anode, the other is the cathode). Through the contact electrodes, an electrical stimulation is directly applied to areas of the deep brain, more peculiarly the basal ganglia. A typical electrical current usable in the context of the invention is pulsed, with a high frequency [between 100 and 200 Hz, the most frequently used being 130 Hz), a pulse width between 60 and 120 μs, a low voltage (below 4V) and a low current (below 2 mA)].

Application of a high frequency electrical stimulation to the basal ganglia is typically approved (at least in the United States and/or in the European Union) and usable in the context of the invention for several movement/motor disorders such as Parkinson's disease, dystonia, epilepsy, Obsessive Compulsive Disorders (OCD) and Tourette's syndrome.

Transcranial Magnetic Stimulation (TMS)

Transcranial Magnetic Stimulation (TMS) is a non-invasive technique that is used or investigated for numerous research and therapeutic applications, including the study of normal and pathological brain functions and the treatment of neural disorders, and which is usable in the context of the invention. TMS uses brief, intense pulses of electric current delivered to a coil placed on the subject's head to generate an electric field in the brain via electromagnetic induction. The induced electric field modulates the neural transmembrane potentials and, thereby, neural activity. The locus of activation in the brain is approximately in the area where the induced electrical field is maximal; this location, in turn, depends on the stimulating coil's geometry and placement. Two electric field spatial features of interest are depth of penetration and focality, which both depend on the coil geometry and are easily determinable by the skilled person. Repetitive TMS (rTMS) is typically used for depression, pain, stroke, etc.

Transcranial Direct Current Stimulation (tDCS)

Transcranial Direct Current Stimulation (tDCS) is a non-invasive technique, usable in the context of the invention, where brain stimulation is performed thanks to a direct current, leading to changes in the cortical excitability. tDCS uses a low-intensity (0.5-2 mA) constant current which is applied directly to the head via two electrodes (anode/cathode) of typically 20-35 cm$^2$. One electrode (reference electrode) can be placed over the forehead (above the supraorbital ridge) and the other (active electrode) can be placed over the contralateral hemisphere, commonly over the motor cortex (M1) or the dorsolateral prefrontal cortex, depending on the design. The duration of the stimulation most often ranges between 20 and 40 minutes. A portion of current penetrates the brain, producing a peak electric field of approximately 0.3 V/m per 1 mA applied. The sustained electric field produced during tDCS modifies the transmembrane neuronal potential and can influence the level of excitability and the responsiveness to synaptic input, and modulates the firing rate of individual neurons. Increased excitability occurs with anodal stimulation, whereas decreased excitability typically occurs with cathodal stimulation.

tDCS is usable for the treatment of autism (Chi et al., *Medical Hypotheses*, 2014, 83, 614-618: *Treating autism by targeting the temporal lobes*), motor rehabilitation after a stroke (Gillick et al., *Frontiers in Human Neuroscience*, 2014, 8(739), 1-9: *Pediatric stroke and tDCS: method for rational individualized dose optimization*), major depressive disorder (Croarkin et al., *Frontiers in Human Neuroscience*, 2014, 8(669), 1-9: *Developmental aspects of cortical excitability and inhibition in depressed and healthy youth: an exploratory study*).

Nanoparticles

Herein described is a nanoparticle or aggregate of nanoparticles for use according to the invention for preventing or treating/for use in prevention or treatment of a neurological disease or at least one symptom thereof in a subject when said nanoparticle or aggregate of nanoparticles is exposed to an electric field, wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Composition of Nanoparticles

Nanoparticle Prepared from a Conductor Material

The nanoparticle prepared from a conductor material is an organic nanoparticle or an inorganic nanoparticle.

Inorganic nanoparticle prepared from a conductor material is typically prepared with a metallic element having a standard reduction potential E° value equal to or above about 0.01, typically when measured at 25° C. and at a pressure of 1 atm in respect to the standard hydrogen electrode (see Table 2 *"reduction reactions having E° values more positive than that of the standard hydrogen electrode"*, 8-25, *Handbook of chemistry and physics*; David R. Lide; 88$^{th}$ Edition), more preferably equal to or above about 0.1, 0.2, 0.4, or 0.5. Typical metallic elements used to prepare the nanoparticles may be selected from Tl, Po, Ag, Pd, Ir, Pt, Au, and a mixture thereof. Preferably, the metallic element usable as conductor material to prepare the nanoparticles is selected from Ir, Pd, Pt, Au, and a mixture thereof.

Organic nanoparticle prepared from a conductor material is typically prepared with an organic material having contiguous sp2 hybridized carbon centers in its structure (i.e. carbon double bond or aromatic cycles comprising heteroatoms, typically N or S, within the aromatic cycle or outside the aromatic cycle). Preferred organic materials are selected from polyaniline, polypyrrole, polyacetylene, polythiophene, polycarbazole, polypyrene, poly(3,4-ethylenedioxythiophene) and/or poly(3,4-ethylenedioxythiophene) polystyrene sulfonate.

Nanoparticle Prepared from a Semiconductor Material

The nanoparticle prepared from a semiconductor material is typically an inorganic nanoparticle. Inorganic nanoparticles are typically prepared with a semiconductor material presenting a relatively small energy band gap (Eg) between its valence and conduction bands. Typically, the semiconductor material has a band gap Eg below 3.0 eV, typically when measured at room temperature (25° C.). In a particular aspect, the material is an intrinsic semiconductor material or an extrinsic semiconductor material as further herein described below.

Intrinsic semiconductor materials typically consist of an element from group IV A of the Mendeleev's periodic table, such as Silicon (Si) or Germanium (Ge), or a mixed composition of elements from groups III and V of the Mendeleev's periodic table, such as AlSb, AlN, GaP, GaN, InP, InN, etc., or a mixed composition of elements from groups II and VI of the Mendeleev's periodic table, such as ZnSe, ZnTe, CdTe, etc.

Extrinsic semiconductor materials typically comprise, or consist of, an intrinsic semiconductor prepared with a high degree of chemical purity, wherein the intrinsic semiconductor material comprises a dopant. In a particular aspect, when the nanoparticle's or nanoparticles' aggregate's extrinsic semiconductor material consists of an element from group IVA of the Mendeleev's periodic table, it is doped with a charge carrier selected from Al, B, Ga, In and P. Such extrinsic semiconductor materials may be either of n-type in which negative charge carriers dominate or of p-type in which positive charge carriers dominate. Typical extrinsic p-type semiconductor material consists of silicon (Si) or germanium (Ge) doped with a charged carrier selected from aluminum (Al), Boron (B), Gallium (Ga) and indium (In); Typical extrinsic p-type semiconductor material consists of silicon (Si) or germanium (Ge) typically doped with phosphorus (P).

Nanoparticle Prepared from an Insulator Material Having a High Relative Dielectric Constant (Relative Permittivity), i.e. Equal to or Above 200

The nanoparticles prepared from, or consisting of, an insulator material having a high relative dielectric constant $\varepsilon_{ijk}$ (also named relative permittivity), are typically prepared with a material having a band gap Eg equal to or above 3.0 eV typically when measured at room temperature (25° C.) and a relative dielectric constant $\varepsilon_{ijk}$ equal to or above 200, which is typically measured between 20° C. and 30° C. and between $10^2$ Hz up to the infrared frequency (see for instance table 12-45 "Permittivity (dielectric constant) of inorganic solid"; Handbook of chemistry and physics; David R. Lide; 88$^{th}$ Edition; Compilation of the static dielectric constant of inorganic solid. K. F. Young and H. P. R. Frederikse. J. Phys. Chem. Ref. Data, Vol. 2, No. 2, 1973).

Such nanoparticles are typically prepared with a dielectric material which is a mixed-metal oxide preferably selected from $BaTiO_3$, $KTaNbO_3$, $KTaO_3$, $SrTiO_3$, $BaSrTiO_3$, etc.

Nanoparticle Prepared from an Insulator Material Having a Low Relative Dielectric Constant (Relative Permittivity), i.e. Equal to or Below 100

The nanoparticles prepared from, or consisting of, an insulator material having a low relative dielectric constant are typically prepared with a material having a band gap Eg equal to or above 3.0 eV typically when measured at room temperature (25° C.) and a relative dielectric constant $\varepsilon_{ijk}$ equal to or below 100, preferably below 50 or below 20, which is typically measured between 20° C. and 30° C. and between $10^2$ Hz up to the infrared frequency, (see for instance table 12-45 "Permittivity (dielectric constant) of inorganic solid"; Handbook of chemistry and physics; David R. Lide; 88$^{th}$ Edition; Compilation of the static dielectric constant of inorganic solid. K. F. Young and H. P. R. Frederikse. J. Phys. Chem. Ref Data, Vol. 2, No. 2, 1973).

Such nanoparticles are typically prepared with a dielectric material which is selected from a metal oxide, a mixed metal oxide, the metallic element of which is from period 3, 5 or 6 of the Mendeleev's periodic table or a lanthanide, and a carbon material. The dielectric material is preferably selected from $Al_2O_3$, $LaAlO_3$, $La_2O_3$, $CeO_2$, $SiO_2$, $SnO_2$, $Ta_2O_5$, $ZrO_2$, $HfO_2$, $Y_2O_3$ and carbon diamond.

The Nanoparticle's or Nanoparticles Aggregate's Shape

As the shape of the particle or aggregate can influence its "biocompatibility", particle or aggregate having a quite homogeneous shape is preferred. For pharmacokinetic reasons, nanoparticles or aggregates being essentially spherical, round or ovoid in shape are thus preferred. Such a shape also favors the nanoparticle's or aggregate's interaction with cells or uptake by cells. Spherical or round shape is particularly preferred.

The shape of the nanoparticle or aggregate of nanoparticles is typically evaluated using transmission electron microscopy (TEM).

The Nanoparticle's or Nanoparticles Aggregate's Dimension or Size

In the spirit of the invention, the terms "nanoparticle" or "nanoparticles' aggregate" refers to a product, in particular a synthetic product, with a size in the nanometer range, typically between 1 nm and 500 nm.

The term "aggregate of nanoparticles" or "nanoparticles' aggregate" refers to an assemblage of nanoparticles strongly, typically covalently, bound to each other.

Transmission electron microscopy (TEM) can be used to measure the size of the nanoparticle or of the aggregate of nanoparticles. As well, dynamic light scattering (DLS) can be used to measure the hydrodynamic diameter of nanoparticles or nanoparticles' aggregates in solution. These two methods may further be used one after each other to compare size measures and confirm said size. A preferred method is DLS (Ref. International Standard ISO22412 Particle Size Analysis—Dynamic Light Scattering, International Organisation for Standardisation (ISO) 2008), whereas the mean hydrodynamic diameter of the nanoparticle or the aggregate of nanoparticles in solution is given in intensity.

Typically, the largest dimension or size is the diameter of a nanoparticle of round or spherical shape, or the longest length of a nanoparticle of ovoid or oval shape.

The largest dimension of a nanoparticle or aggregate as herein defined is typically between about 2 nm and about 250 nm, preferably between about 4 nm or 10 nm and about 100 nm or about 200 nm, even more preferably between about 10 nm and about 150 nm.

The Nanoparticles' or Aggregates of Nanoparticles' Biocompatible Coating

In a preferred embodiment, the nanoparticle or nanoparticles' aggregate used in the context of the present invention to prepare a composition of interest can be coated with a biocompatible material selected from an agent exhibiting stealth property. Agent exhibiting stealth properties may be an agent displaying a steric group. Such a group may be selected for example from polyacrylate; polyacrylamide (poly(N-isopropylacrylamide)); polycarbamide; a biopolymer; a polysaccharide such as dextran or xylan; and collagen. In another preferred embodiment, the nanoparticles or nanoparticles' aggregates can be coated with a biocompatible material selected from an agent allowing interaction with a biological target. Such an agent can typically bring a positive or a negative charge on the nanoparticle's or nanoparticles' aggregate's surface. An agent forming a positive charge on the nanoparticle's or nanoparticles' aggregate's surface can be for example aminopropyltriethoxisilane or polylysine. An agent forming a negative charge on the nanoparticle's or nanoparticles' aggregate's surface can be for example a phosphate (for example a polyphosphate, a metaphosphate, a pyrophosphate, etc.), a carboxylate (for example citrate or dicarboxylic acid, in particular succinic acid) or a sulphate.

In a preferred embodiment, the nanoparticle or aggregate of nanoparticles used in the context of the present invention presents a hydrophilic neutral surface charge or is coated with a biocompatible material (i.e. a coating agent) selected from a hydrophilic agent conferring a neutral surface charge to the nanoparticle. Indeed, when the nanoparticles of the present invention are administered to a subject, nanoparticles presenting a hydrophilic neutral surface charge or nanoparticles coated with a biocompatible agent selected from a hydrophilic agent conferring a neutral surface charge to the nanoparticles are particularly advantageous to optimize the use of the nanoparticles for treating a neurological disease or at least one symptom thereof when exposed to an electrical stimulus/field.

A hydrophilic agent conferring neutral surface charge to the nanoparticle or nanoparticles' aggregate may be an agent displaying a functional group selected from an alcohol (R—OH), an aldehyde (R—COH), a ketone (R—CO—R), an ester (R—COOR), an acid (R—COOH), a thiol (R—SH), a saccharide (glucose, fructose, ribose for instance), an anhydride (RCOOOC—R), and a pyrrole. The hydrophilic agent conferring a neutral surface charge to the nanoparticle or nanoparticles' aggregate can be a monomer, a dimer, an oligomer, a polymer or a copolymer. When the agent is an oligomer, it may be an oligosaccharide such as a cyclodextrin. When the agent is a polymer, it may be a polyester (such as a poly(lactic acid) or a polyhydroxyalkanoic acid), a polyether, a polyethylene oxide, a polyethylene glycol, a polyvinylalcohol, a polycaprolactone, a polyvinylpyrrolidone, a polysaccharide such as a cellulose, a polypyrrole, etc.

In addition, a hydrophilic agent conferring neutral surface charge to the nanoparticle or nanoparticles' aggregate may be an agent displaying specific groups (R—) able to interact with the surface of the nanoparticle or aggregate of nanoparticles. R is typically selected from a thiol, a silane, a carboxylic and a phosphate group.

When the nanoparticle or aggregate of nanoparticles is a conductor or a semiconductor and a metallic nanoparticle, R is preferably a thiol, a thioether, a thioester, a dithiolane or a carboxylic group. Preferably, the hydrophilic neutral coating agent is selected from a thioglucose, a 2-mercaptoethanol, a 1-thioglycerol, a thiodiglycol and a hydroxybutyric acid.

When the nanoparticle or aggregate of nanoparticles is an insulator, and an oxide or a mixed-oxide nanoparticle, R is preferably a silane or a phosphate group. Preferably, the hydrophilic neutral coating agent is a hydroxymethyltriethoxysilane, a fructose 6-phosphate or a glucose 6-phosphate compound. A hydrophilic agent conferring neutral surface charge to the nanoparticle or nanoparticles' aggregate may be a zwitterionic compound such as an amino acid, a peptide, a polypeptide, a vitamin or a phospholipid.

The surface charge of a nanoparticle or nanoparticles' aggregate is typically determined, as well known by the skilled person, by zeta potential measurements, typically in water for a nanoparticles concentration between 0.2 and 10 g/L, for a pH between 6 and 8, and typically by adding electrolytes at concentrations in water between 0.001 and 0.2 M, for example 0.01 M or 0.15 M. Under the above defined conditions, the surface charge of the nanoparticle or aggregate of nanoparticles is typically comprised between −10 mV and +10 mV (corresponding to a neutral surface charge), between −20 mV and +20 mV, or between −35 mV and +35 mV.

A full biocompatible coating of the nanoparticle or aggregate may be advantageous in the context of the present invention in order to avoid any electrical charge on the nanoparticle's surface, when the nanoparticle presents a hydrophilic neutral surface charge. The "full coating" implies the presence of a very high density/compactness of biocompatible molecules able to create at least a complete monolayer on the surface of the particle.

The biocompatible coating allows in particular the nanoparticle's stability in a fluid, such as a physiological fluid (blood, plasma, serum, etc.) or any isotonic media or physiologic medium required for a pharmaceutical administration.

Stability may be confirmed by dry extract quantification using a drying oven and measured on a nanoparticle suspension prior and after filtration, typically on a 0.45 µm filter.

Advantageously, the coating preserves the integrity of the particle in vivo, ensures or improves the biocompatibility thereof, and facilitates an optional functionalization thereof (for example with spacer molecules, biocompatible polymers, targeting agents, proteins, etc.).

The biocompatible nanoparticle or aggregate of nanoparticles of the invention should neither dissolve and release toxic species following in vivo administration (i.e. at physiological pH) nor present redox behavior in absence of electrical stimulation.

Another particular object herein described relates to a composition, in particular a pharmaceutical composition, comprising nanoparticles and/or nanoparticles' aggregates such as defined hereinabove, preferably together with a pharmaceutically acceptable carrier or vehicle.

In particular, herein described is a composition for use for preventing or treating/for use in prevention or treatment of a neurological disease as herein described or at least one symptom thereof in a subject exposed to an electric field, wherein the composition comprises, or consists of, nanoparticles and/or nanoparticles' aggregates and a pharmaceutically acceptable support, and wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100 as herein above explained.

In a preferred aspect, the composition comprises, or consists of, at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100.

In a particular aspect, the composition can comprise the nanoparticles or nanoparticles' aggregates of the invention together with a therapeutic agent. The therapeutic agent can be selected from any drug used in a neurological disorder treatment. The therapeutic agent is typically selected from antipsychotics, anti-dopaminergics, dopaminergics, anti-cholinergics, cholinergics, anti-glutamatergics, glutamatergics, acetylcholinesterase inhibitors, N-methyl D-aspartate (NMDA) receptor antagonists, gamma-amino butyric acid (GABA) agonists, botulinum toxin, anti-dystonic drugs, anti-epileptic drugs, anticonvulsants, mood stabilizers, antidepressants and sedatives.

The composition can be in the form of a solid, liquid (particles in suspension), aerosol, gel, paste, and the like. Preferred compositions are in a liquid or a gel form. Particularly preferred compositions are in liquid form.

The pharmaceutically acceptable support or carrier which is employed can be any classical support for the skilled person, such as for example a saline, isotonic, sterile, buffered solution, a non-aqueous vehicle solution and the like.

The composition can also comprise stabilizers, sweeteners, surfactants, polymers and the like.

It can be formulated for example as ampoule, aerosol, bottle, tablet, capsule, by using techniques of pharmaceutical formulation known by the skilled person.

The nanoparticles or nanoparticles' aggregates of the invention can be administered to the subject using different possible routes such as intra-cranial, intra venous (IV), airways (inhalation), intra-thecal, intra-ocular or oral route (per os), preferably using intra-cranial or intra-thecal.

Repeated injections or administrations of nanoparticles can be performed, when appropriate.

The herein described nanoparticles or nanoparticles' aggregates and compositions comprising such nanoparticles or nanoparticles' aggregates are for use in a subject, typically for use in an animal, preferably in a mammal, even more preferably in a human being, typically a human patient, whatever its age or sex.

Typical quantity(ies) of nanoparticles or aggregates of nanoparticles to be administered in the cerebral cortex of the subject is(are) between $10^5$ and $10^{15}$, preferably between $10^7$ and $10^{14}$, more preferably between $10^9$ and $10^{12}$. Also typical quantity(ies) of nanoparticles or aggregates of nanoparticles to be administered in the cerebral cortex of the subject is(are) between $10^2$ and $10^{12}$ nanoparticles or aggregates of nanoparticles per cm$^3$.

Typical quantity(ies) of nanoparticles or aggregate of nanoparticles to be administered in the deep brain of the subject is(are) between $10^4$ and $10^{14}$, preferably between $10^6$ and $10^{12}$, more preferably between $10^8$ and $10^{11}$. Also typical quantity(ies) of nanoparticles or aggregates of nanoparticles to be administered in the deep brain of the subject is(are) between $10^1$ and $10^{11}$ nanoparticles or aggregates of nanoparticles per cm$^3$.

In the context of the invention, exposing nanoparticles or nanoparticles' aggregates to an electric field/stimulus is equivalent to exposing a subject who has been administered with nanoparticles or nanoparticles' aggregates to an electric field/stimulus.

Also herein described is a method for preventing or treating a neurological disease or at least one symptom thereof in a subject, wherein the method comprises a step of administering anyone of the herein described nanoparticles or nanoparticles' aggregates to the subject and a step of exposing said subject to an electric field/stimulus.

A further object herein described relates to a kit comprising at least two distinct nanoparticles and/or at least two distinct nanoparticles' aggregates as herein described, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100 as herein described.

In a particular embodiment, the kit comprises, in distinct containers, distinct nanoparticles and/or nanoparticles aggregates as herein described (which are intended to be contacted, typically mixed, either in situ, i.e. on the target site, or in vitro or ex vivo before deposition of the mixture on the target site).

A further object relates to a kit further comprising at least one additional therapeutic agent, distinct from the nanoparticles or nanoparticles aggregates as herein described, such as an antipsychotic, anti-dopaminergic, dopaminergic, anti-cholinergic, cholinergic, anti-glutamatergic, glutamatergic, acetylcholinesterase inhibitor, N-methyl D-aspartate (NMDA) receptor antagonist, gamma-amino butyric acid (GABA) agonist, botulinum toxin, anti-dystonic drug, anti-epileptic drug, anticonvulsants, mood stabilizer, antidepressant and sedative, that the skilled person of the art will be able to select depending on the nature of the targeted disease.

Also herein described is the use, in vivo, in vitro or ex vivo, of such a kit in a method for preventing or treating a neurological disease as herein described or at least one symptom thereof in a subject. Also herein disclosed is a kit as herein described for use in prevention or treatment of a neurological disease or of at least one symptom thereof in a subject.

The present invention aims at treating a neurological disease or at least one symptom thereof thanks to the use of nanoparticles or nanoparticles' aggregates exposed to an electrical stimulus/field.

At the neuron level, nanoparticles have been described to enhance or inhibit electrical excitability of neurons. For instance, zinc oxide, carbon nanotubes and gold nanoparticles were found to enhance electrical excitability of neurons whereas, copper oxide, silver, carbon black, iron oxide and titanium oxide were found to inhibit electrical excitability of neurons (Polak P & Shefi O. *Nanomedicine: Nanotechnology, Biology and Medicine* 11 (2015) 1467-1479, *Nanometric agents in the service of neuroscience: Manipulation of neuronal growth and activity using nanoparticles*).

Systemic influence studies on neuronal systems of coated silver nanoparticles (cAgNP)—using amphiphilic polymer polyethylene glycol—[cAgNP with hydrodynamic diameter of 13 nm±2 nm (dynamic light scattering technique) and zeta potential of −69 mV (Zetasizer Nano) in pure water]) showed that the nanoparticles induced changes in mechanism affecting excitability. Besides, neuron network simulation showed that locally cAgNP-induced changes result in changes in network activity in the entire network, indicating that local application of cAgNP may influence the activity throughout the network (Busse M. et al. *International Journal of Nanomedicine* 2013:8 3559-3572, *Estimating the modulatory effects of nanoparticles on neuronal circuits using computational upscaling*).

Also, increased excitability of neurons associated with intracellular gold nanoparticles has been described to potentially have deleterious effects on neurons under pathological conditions such as seizure (Jung S, et al. *PLOS ONE* 2014, 9(3) e91360, *Intracellular gold nanoparticles increase neuronal excitability and aggravate seizure activity in the mouse brain*).

The nanoparticles or nanoparticles' aggregates of the present invention are, when exposed to an electric field/stimulus, for use for preventing or treating/for use in prevention or treatment of a neurological disease or at least one symptom thereof, by normalizing synchronization of oscillations within and/or between neuronal networks within and/or between distinct regions of the brain.

Figure 3:
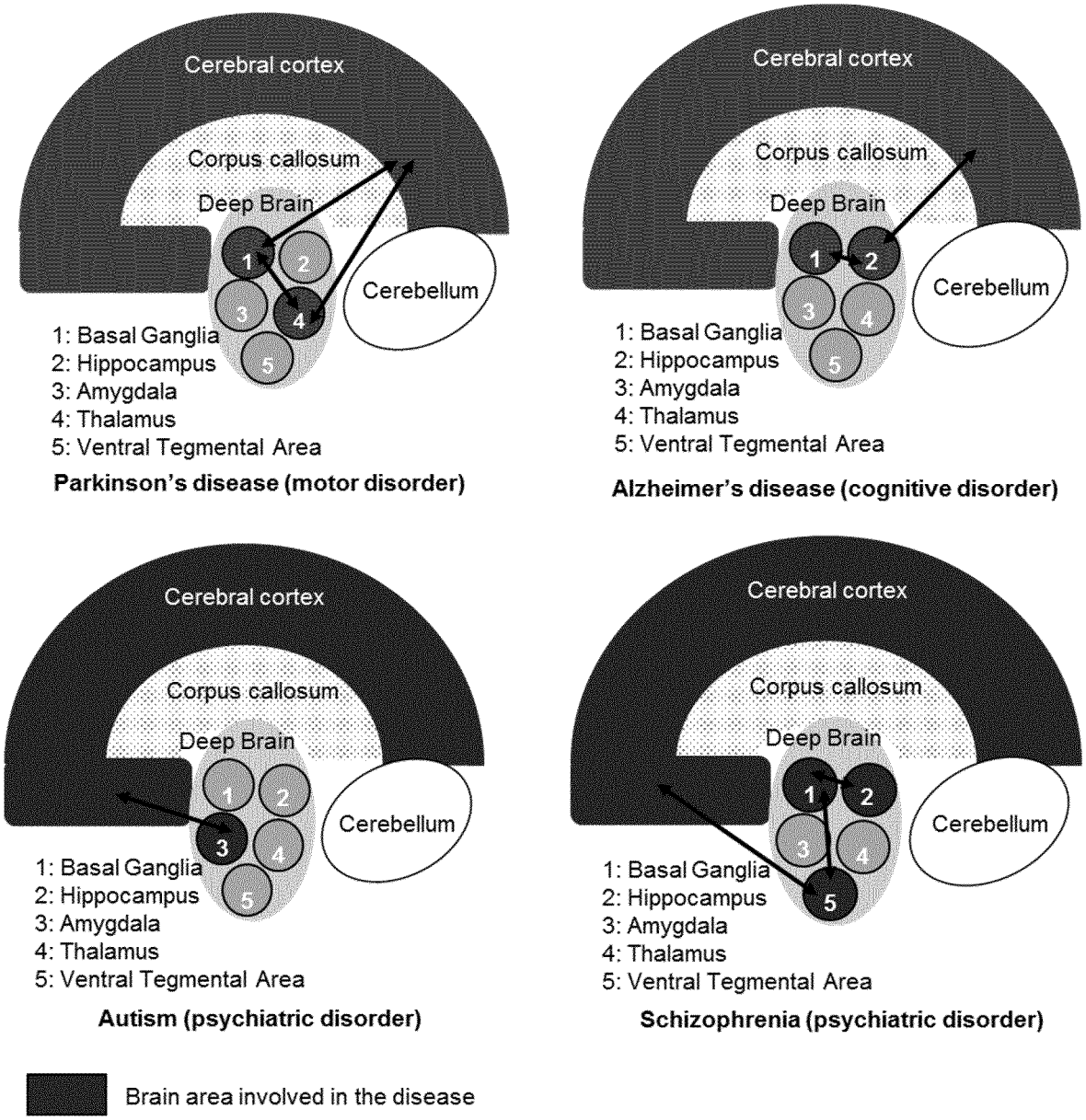
Figure 4:
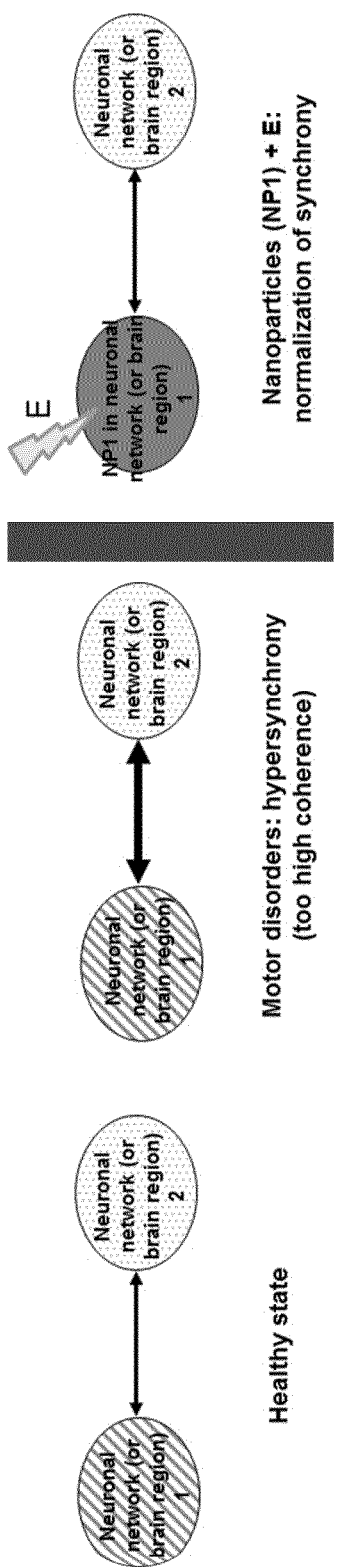
Figure 5:
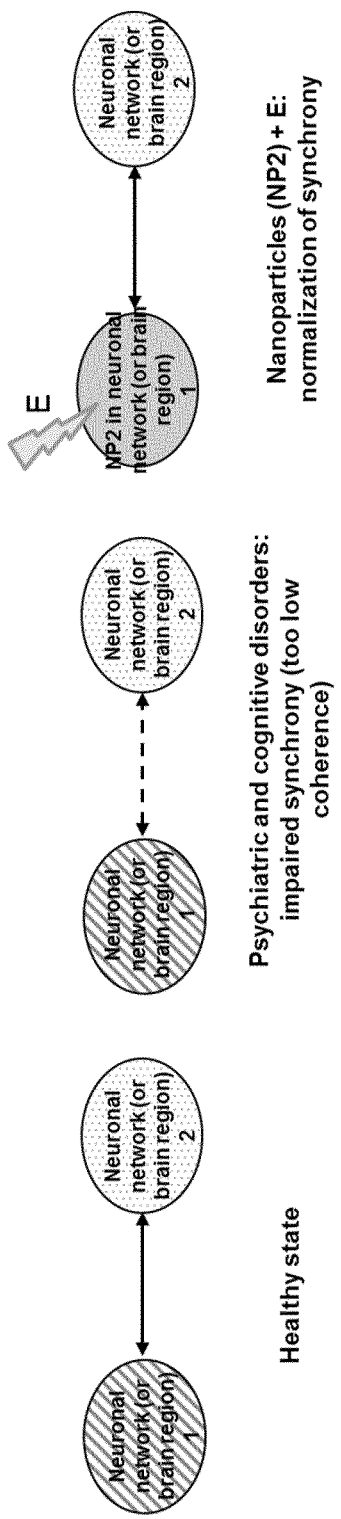

As illustrated in FIGS. 2 and 3, communication within and/or between distinct regions of the brain is affected in neurological disease. According to the neurological disorder and associated symptoms, exposition of specific area of the brain to nanoparticles of the present invention (see table 2), will, when combined to an electrical stimulus, improve communication via normalization of the synchronization of oscillations within and/or between neuronal networks within and/or between distinct regions of the brain (i.e. normalization of the coherence) (FIGS. 4 and 5 and Table 2).

TABLE 2

Combination of a type of nanoparticle with a type of electric stimulation technique for the treatment of different neurological disorders.

| Type of nanoparticles (or aggregate of nanoparticles) | Type of Material | Target disease | Target area | Type of stimulation |
|---|---|---|---|---|
| Nanoparticle 1 (NP1) | Insulating - dielectric constant ≤100<br>Insulating - dielectric constant ≥200<br>Semi-conductor<br>Conductor | Motor Disorders | Deep brain | Deep Brain Stimulation (DBS) |
| NP1 | Insulating - dielectric constant ≤100<br>Insulating - dielectric constant ≥200<br>Semi-conductor<br>Conductor | Motor Disorders | Cerebral cortex | Transcranial Electric Stimulation (TES) and Transcranial Magnetic Stimulation (TMS) |
| Nanoparticle 2 (NP2) | Conductor<br>Semi-conductor<br>Insulating - dielectric constant ≥200<br>Insulating - dielectric constant ≤100 | Psychiatric and cognitive disorders | Deep brain | DBS |
| NP2 | Conductor<br>Semi-conductor<br>Insulating - dielectric constant ≥200<br>Insulating - dielectric constant ≤100 | Psychiatric and cognitive disorders | Cerebral cortex | TES and TMS |

As easily understandable by the skilled person, effects of electrical stimulation on neural networks are related to the depth of penetration and spatial resolution of the electric field within the targeted brain area. Poor spatial resolution and depth of penetration are important drawback of electrical stimulation. The presence of nanoparticles or aggregates of nanoparticles of the invention now advantageously allows an enhanced spatial resolution (focality) of the electric field where the nanoparticles are localized and an enhanced depth of penetration of electrical current (increasing its therapeutic effect). The presence of nanoparticles or nanoparticles' aggregates in the targeted tissue also allows a decrease of the applied/induced electrical stimulus threshold required for neuronal stimulation, i.e. it decreases the values of the applied parameters like current, voltage, pulse width and/or frequency. This effect in addition reduces the potential toxicity related to the applied/induced electrical current. This may also have technological impacts, like increasing the shelf life of internal pulse generator (IPG) battery or modifying (decreasing) the size and geometry of DBS electrodes.

The examples which follow and their corresponding figures illustrate the invention without limiting the scope thereof.

FIGURES

FIG. 1. Schematic representation of the brain (sagittal plane).

FIG. 2. Hypersynchrony and impaired synchrony between two neuronal networks.

FIG. 3. Brain areas involved in various neurological diseases.

FIG. 4. Effect of nanoparticles (NP1) when exposed to an electric field (E) on normalization of hypersynchrony (motor disorders).

FIG. 5. Effect of nanoparticles (NP2) when exposed to an electric field (E) on normalization of impaired synchrony (psychiatric and cognitive disorders).

Figure 6:
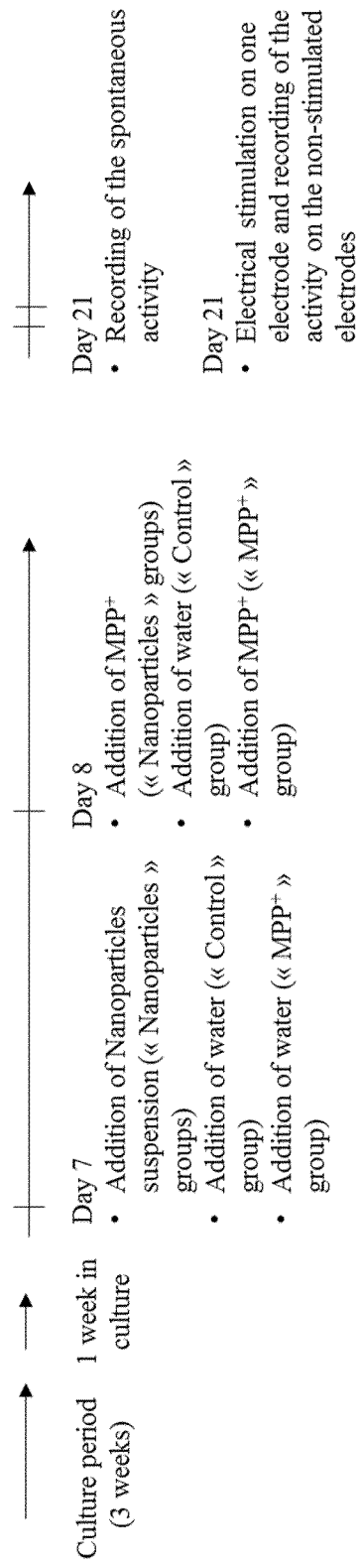

FIG. 6. Experimental scheme of induction of Parkinson's disease with MPP$^+$ treatment and electrical activity recording.

The mouse ventral midbrain/cortex co-cultures were prepared from E14.5 NMRI mice and cultured on 48 well MEAs for 3 weeks (culture period). The cultures were treated after 7 days in culture (day 7) with the nanoparticles' suspensions ("nanoparticles" groups) or water ("control" group and "MPP$^+$" group) and at day 8 with MPP+ (20 µM) ("nanoparticles" groups and "MPP$^+$" group) or water ("control" group). The spontaneous activity was recorded at day 21. After the recording at day 21, the cultures were electrically stimulated on one electrode and recording of the activity was performed on the non-stimulated electrodes.

Figure 7:
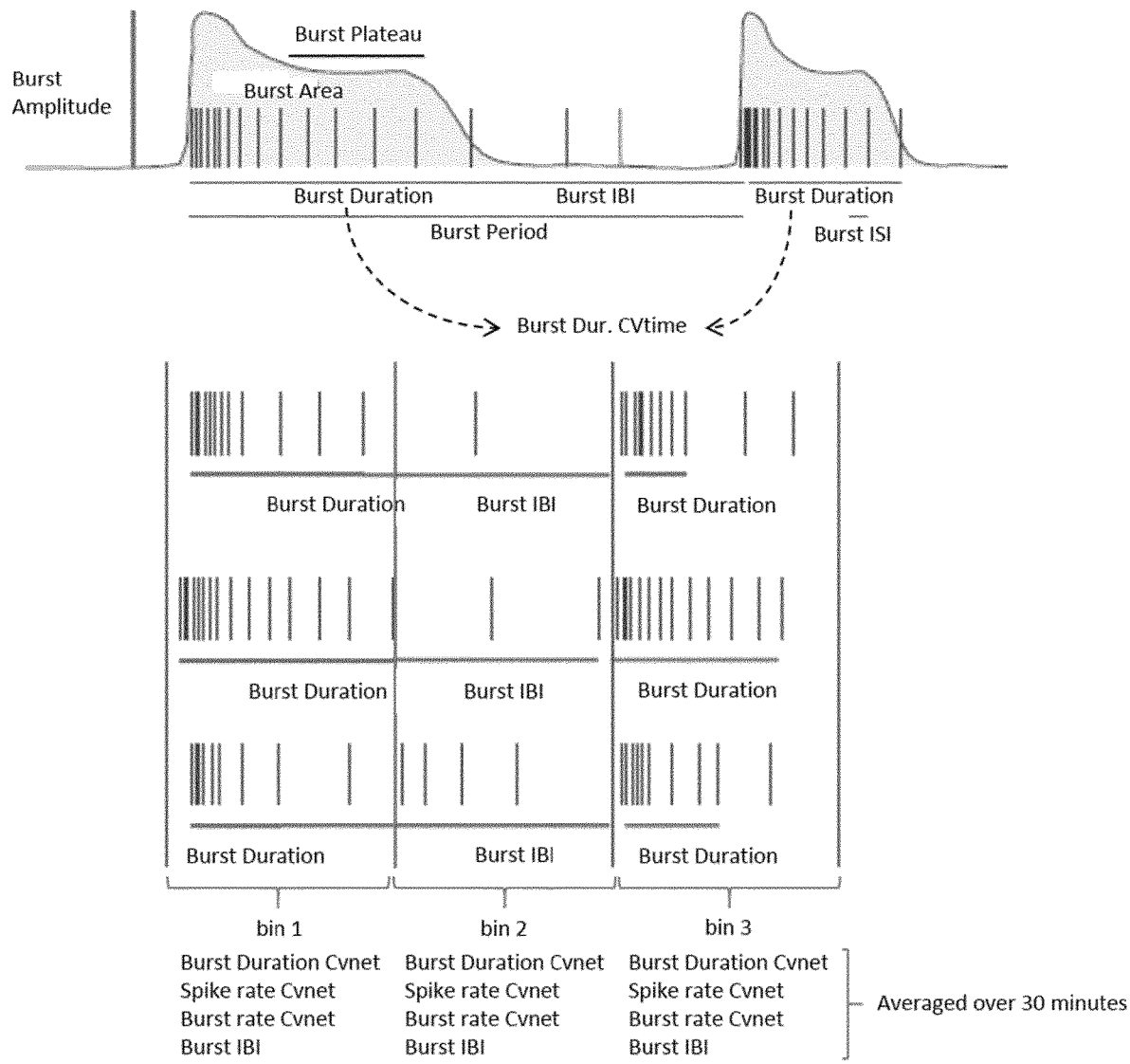

FIG. 7. Scheme of two simplified bursts outlining some of the parameters that can be extracted from the electrical activity recording. Parameters describing general activity (spike, burst, inter burst interval (IBI) and burst period) and burst structure (burst duration, burst plateau, burst amplitude, burst inter spike interval (ISI) and burst area) are indicated. Standard deviations (SD) of these parameters are measures for regularity of general activity and burst structure respectively. Coefficient of variation in time (CVtime) reflects the temporal regularity of the activity pattern of each unit. CVtime is calculated by the ratio of parameter's standard deviation and mean. Coefficient of variation among the network (CVnet) reflects synchronization among neurons within the network. CVnet is calculated by the ratio of parameter's standard deviation by mean over the network. Large CVnet values imply a wide range of variation in the activity across the network, meaning less synchronization.

Figure 8:
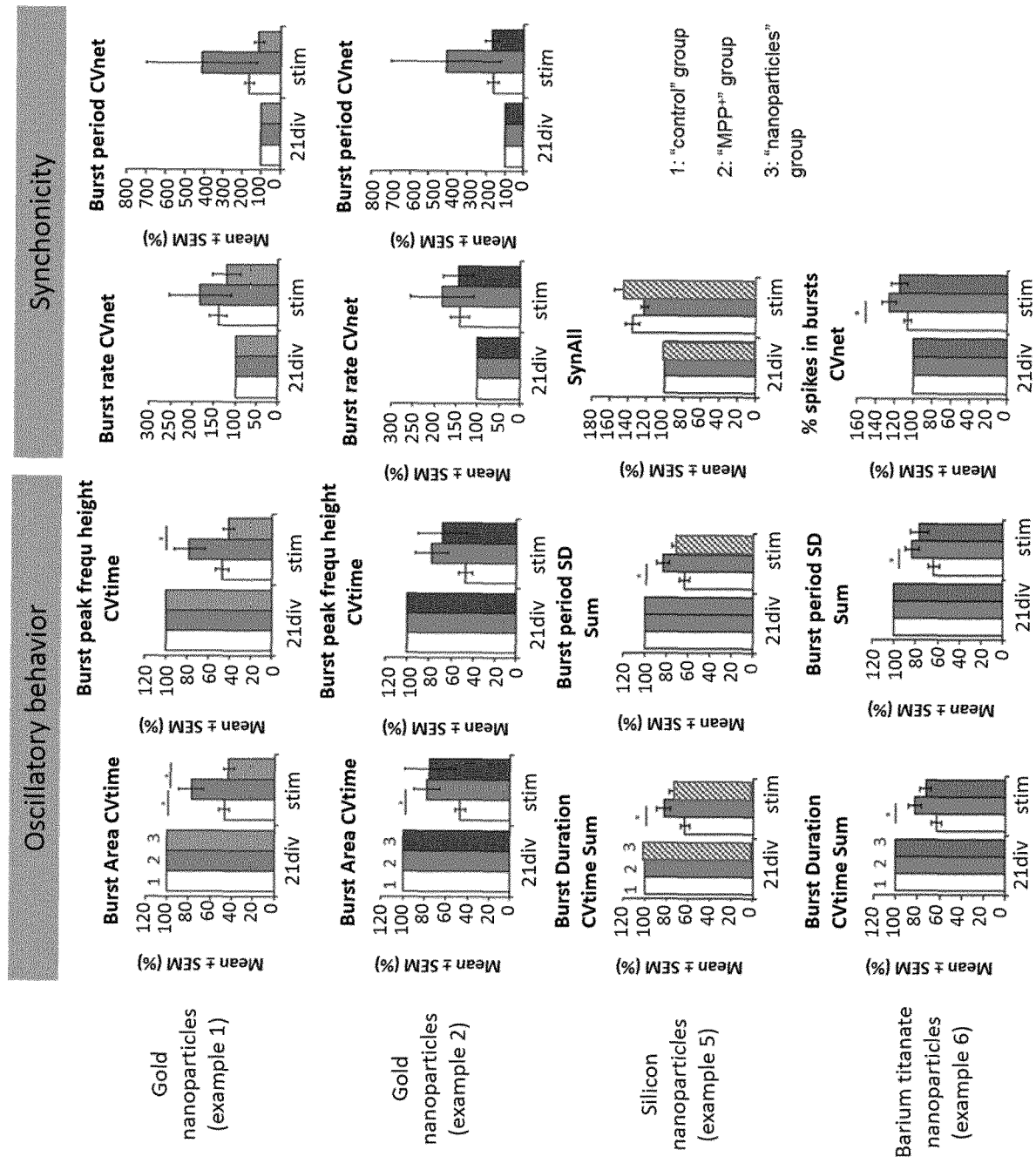

FIG. 8. Functional effects observed in "nanoparticles" groups under electrical stimulation compared to "control" group (under electrical stimulation) and "MPP+" group (under electrical stimulation) on midbrain/cortex network activity. All MPP+-induced functional effects on network activity under electrical stimulation in the presence or not of the tested nanoparticles as well as "control" group (under electrical stimulation), were normalized to the "pre-stimulated" activity, i.e. the activity measured at day 21, set at 100% for each experiment. The data show MPP+-induced functional effects under electrical stimulation and demonstrate the prevention/rescue efficacy of the nanoparticles of the invention under electrical stimulation (i.e. ability to prevent/rescue functional effects to a level similar to that of the "control" group).

Figure 9:
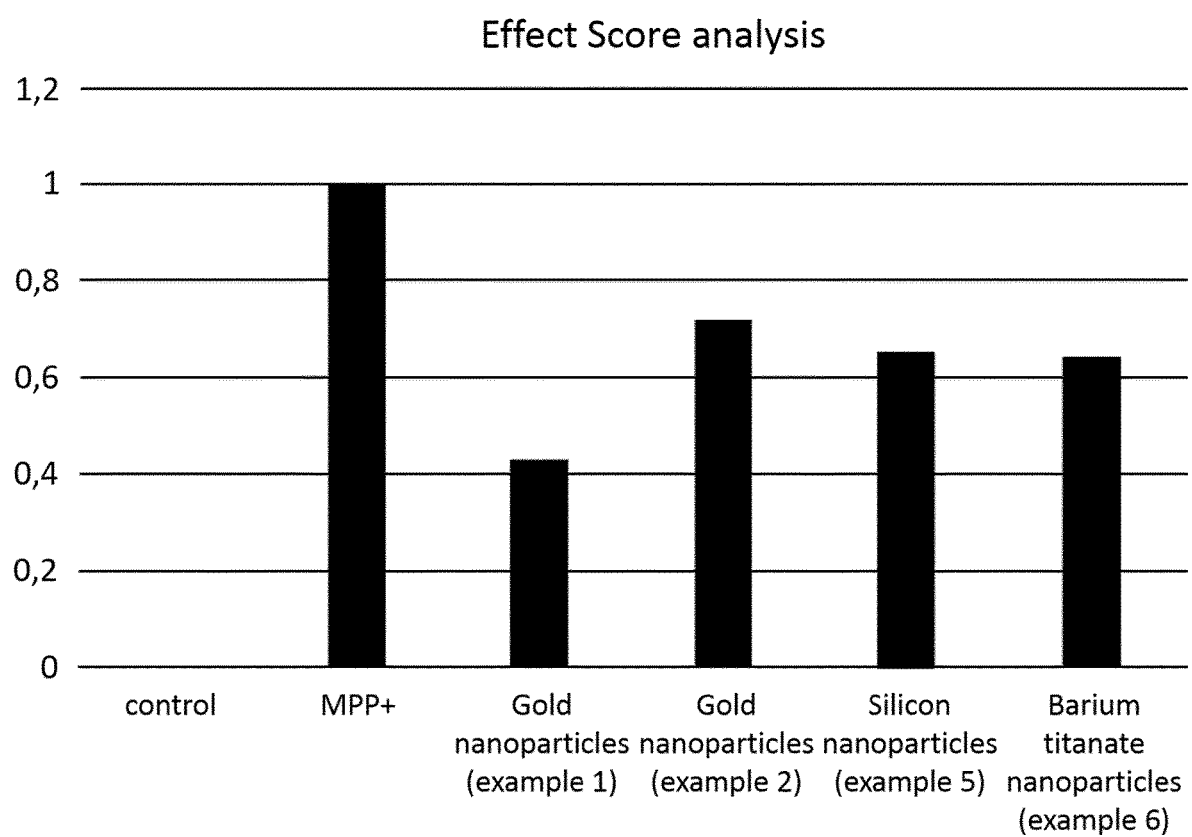

FIG. 9. Effect Score analysis for the "nanoparticles" groups, "control" group (Effect Score=0) and "MPP+" group (Effect Score=1).

Figure 10:
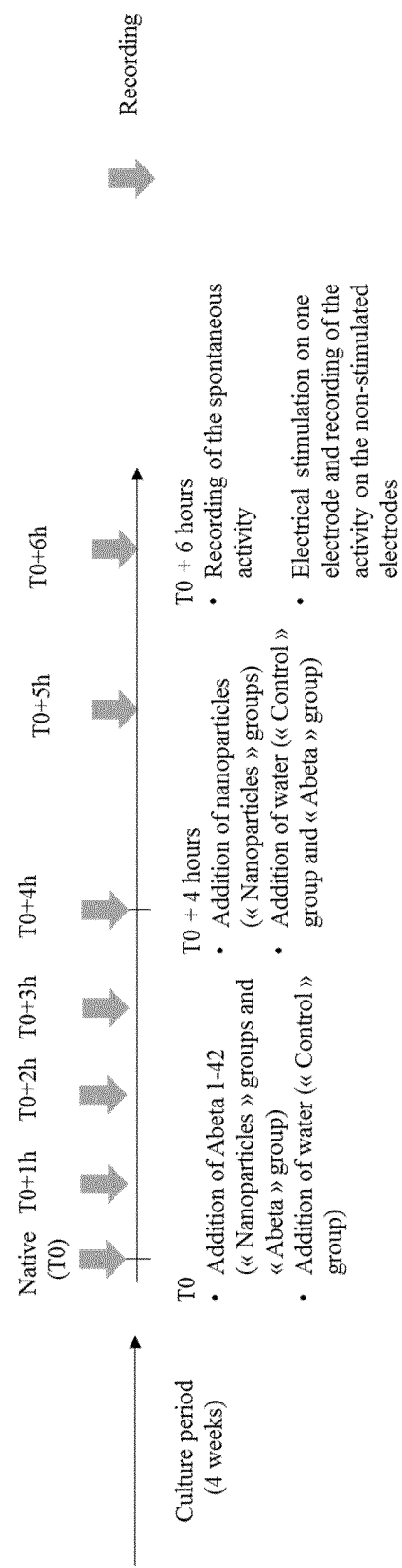

FIG. 10. Experimental scheme of induction of Alzheimer's disease with amyloid beta 1-42 (Abeta 1-42), treatment and electrical activity recordings. After 4 weeks in cultures (culture period), Abeta 1-42 (100 nM) ("nanoparticles" group and "Abeta" group) or water ("control" group) (T0) were added to the neuronal network. Four (4) hours later, the nanoparticles suspensions ("nanoparticles" groups), or water ("control" group and "Abeta" group) were added. The spontaneous activity was recorded as follow:

at T0 (prior addition of Abeta 1-42)
at T0+1 h, T0+2 h, T0+3 h, T0+4 h (prior to nanoparticles or water addition), T0+5 h, and T0+6 h.

Figure 11:
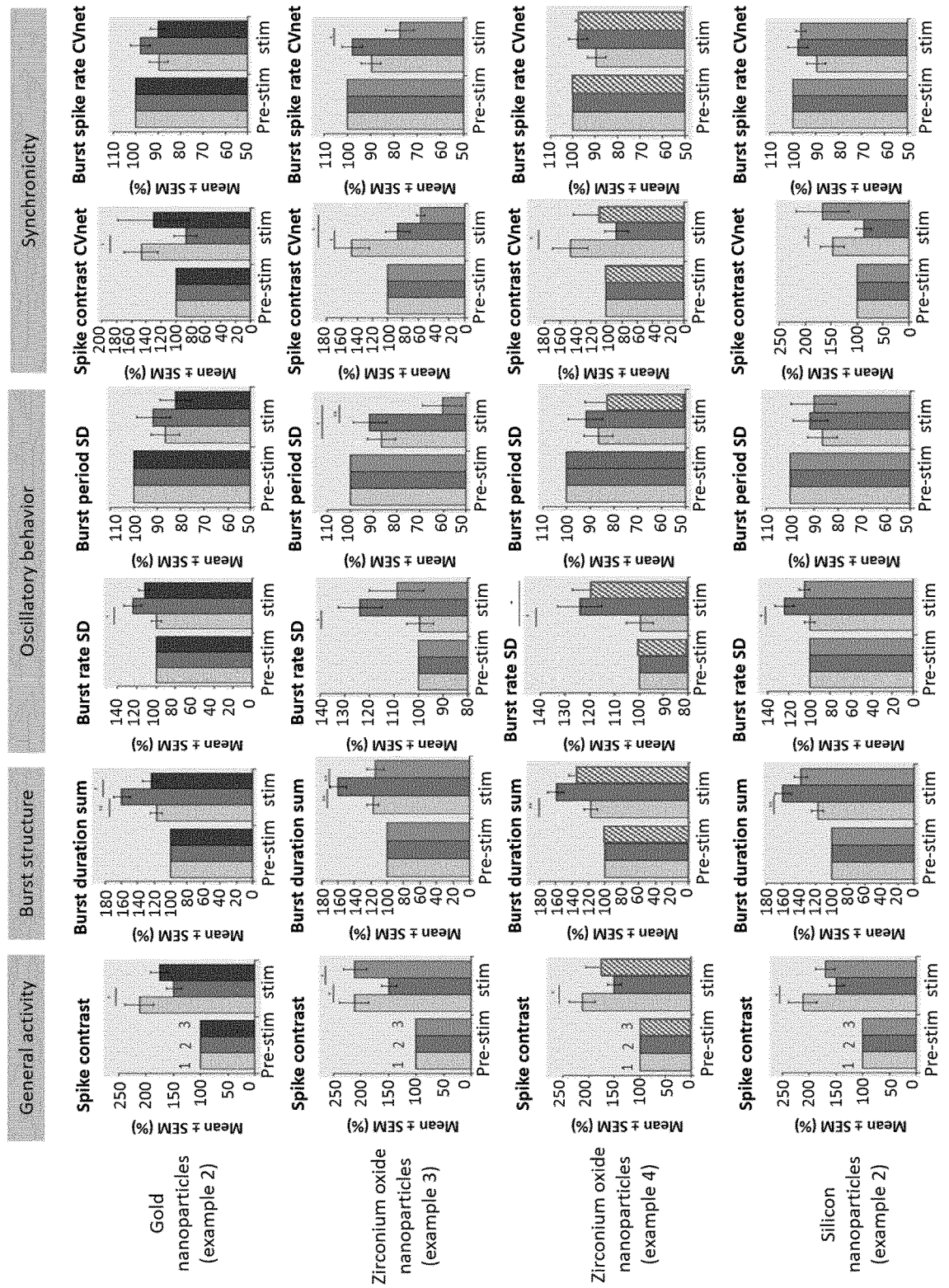

FIG. 11. Functional effects observed in "nanoparticles" groups under electrical stimulation compared to "control" group (under electrical stimulation) and "Abeta 1-42" group (under electrical stimulation) on cortex network activity. All Abeta 1-42-induced functional effects on network activity under electrical stimulation in the presence or not of the tested nanoparticles, as well as "control" group (under electrical stimulation), were normalized to the "pre-stimulated" activity, i.e. the activity measured at T0+6 hours, set at 100% for each experiment.

The data show Abeta 1-42 functional effects under electrical stimulation and demonstrate the rescue efficacy allowed by the nanoparticles of the invention under electrical stimulation (i.e. ability to rescue functional effects to a level similar to that of the "control" group).

Figure 12:
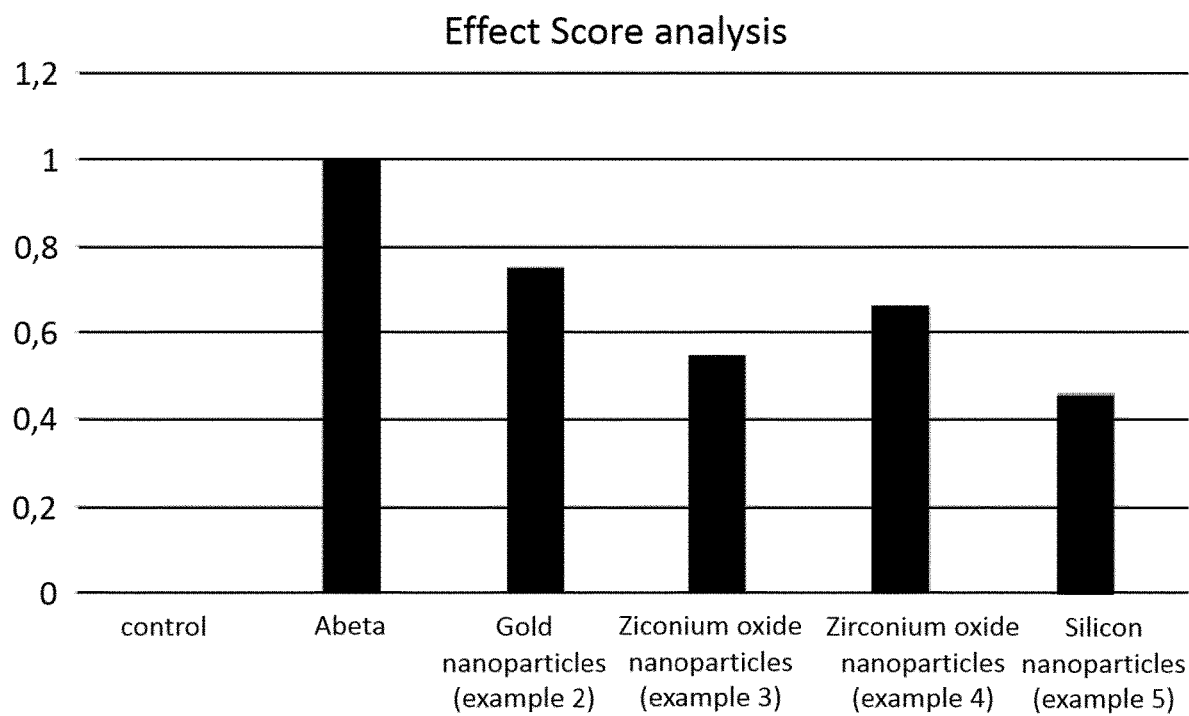

FIG. 12. Effect Score analysis for the "nanoparticles" groups, "control" group (Effect Score=0) and "Abeta" group (Effect Score=1).

EXAMPLES

Simulation

Simulation can be used to assess the effect on neuronal network(s) of nanoparticles exposed to an electrical stimulus (electric field).

In Vitro Studies of Neurons

At the neuron level, Patch clamp technique is very useful for detecting action potentials, as it allows simultaneous direct measurement and control of membrane potential of a neuron.

This technique is used to assess the effects of nanoparticles on a single neuron.

In Vitro Studies of a Network of Neurons

Multi-electrode arrays (MEAs) permit stimulation and recording of a large number of neurons (neuronal network). Dissociated neuronal cultures on MEAs provide a simplified model in which network activity can be manipulated with electrical stimulation sequences through the array's multiple electrodes. This technique is very useful to assess physiologically relevant questions at the network and cellular levels leading to a better understanding of brain function and dysfunction.

Dissociated neuronal cultures coupled to MEAs are indeed widely used to better understand the complexity of brain networks. In addition, the use of dissociated neuronal assemblies allows the manipulation and control of the network's connectivity. The use of dissociated neuronal cultures coupled to MEA allows the design of experiments where neurons can be extracellularly stimulated by mean of electrical pulses delivered through the same electrodes of the device. In this way, it becomes reasonable to investigate how the emerging neuronal dynamics can be modulated by the electrical stimulation, and, consequently, whether the underlying functional connectivity is modified or not (Poli D. et al, *Frontiers in Neural Circuits,* 2015, 9 (article 57), 1-14: *Functional connectivity in in vitro neuronal assemblies*).

The MEA system enables non-invasive, long-lasting, simultaneous extracellular recordings from multiple sites in the neuronal network in real time, increasing spatial resolution and thereby providing a robust measure of network activity. The simultaneous gathering of action potential and field potential data over long periods of time allows the monitoring of network functions that arise from the interaction of all cellular mechanisms responsible for spatio-temporal pattern generation (Johnstone A. F. M. et al., *Neurotoxicology* (2010), 31: 331-350, *Microelectrode arrays: a physiologically based neurotoxicity testing platform for the 21$^{st}$ century*). Compared to patch-clamp and other single electrode recording techniques, MEA measures responses of a whole network, integrating global information on the interaction of all receptors, synapses and neuronal types which are present in the network (Novellino A. et al., *Frontiers in Neuroengineering.* (2011), 4(4), 1-14, *Development of micro-electrode array based tests for neurotoxicity: assessment of interlaboratory reproducibility with neuroactive chemicals*.). As such, MEA recordings have been employed to understand neuronal communication, information encoding, propagation, and processing in neuronal cultures (Taketani, M., and Baudry, M. (2006). *Advances in Network Electrophysiology*. New York, N.Y.: Springer; Obien et al., *Frontiers in Neurosciences,* 2015, 8(423): *Revealing neuronal functions through microelec-* trode array recordings). The MEA technology is a sophisticated phenotypic high-content screening method to characterize functional changes in network activity in electrically active cell cultures and it is very sensitive to neurogenesis, as well as neuroregenerative and neurodegenerative aspects. Moreover, neuronal networks grown on MEAs are known as being capable of responding to neuroactive or neurotoxic compounds in approximately the same concentration ranges that alter functions of an intact mammalian nervous system (Xia et al., *Alcohol*, 2003, 30, 167-174: *Histiotypic electrophysiological responses of cultured neuronal networks to ethanol*; Gramowski et al., *European Journal of Neuroscience*, 2006, 24, 455-465: *Functional screening of traditional antidepressants with primary cortical neuronal networks grown on multielectrode neurochips*; Gramowski et al., *Frontiers in Neurology*, 2015, 6(158): *Enhancement of cortical network activity in vitro and promotion of GABAergic neurogenesis by stimulation with an electromagnetic field with 150 MHz carrier wave pulsed with an alternating 10 and 16 Hz modulation*).

This technique is used to assess the effect of nanoparticles on neuronal network(s).

In Vivo Studies of a Network of Neurons

An appropriate animal model is considered to assess the effect on neuronal networks of animals of nanoparticles of the invention when exposed to an electrical stimulus.

For instance, mouse models of Parkinson's disease are used to assess the effects of nanoparticles stimulated by tDCS (transcranial Direct Current Stimulation) on the relief of behavior impairment (motor disorders). Also, rat models of Alzheimer's disease are used to assess the effects of nanoparticles stimulated by tDCS on the spatial learning and memory dysfunction (cognitive disorders) of animals.

Example 1

Nanoparticles Prepared with a Conductor Material: Synthesis of Gold Nanoparticles Coated with a Biocompatible Coating Having a Neutral Surface Charge Gold nanoparticles were synthesized by reducing a gold chloride salt ($HAuCl_4$) with a capping agent (sodium citrate) (protocol was adapted from G. Frens Nature Physical Science 241 (1973) 21). In a typical experiment, $HAuCl_4$ solution was heated to boiling. Subsequently, sodium citrate solution was added. The resulting solution was maintained under boiling for an additional period of 5 minutes.

A 0.22 µm filtration (filter membrane: poly(ether sulfone) (PES)) of the nanoparticles' suspension was performed and gold concentration in suspension was determined by a UV-visible spectroscopy assay at 530 nm.

A surface coating was performed using α-methoxy-ω-mercaptopoly(ethylene glycol) 20 kDa ("thiol-PEG20 kDa"). A sufficient amount of "thiol-PEG 20 kDa" was added to the nanoparticles' suspension to reach at least half a monolayer coverage (2.5 molecules/$nm^2$) on the gold nanoparticle surface. pH was adjusted between 7 and 7.2, and the nanoparticles' suspension was stirred overnight.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The hydrodynamic diameter of the so obtained biocompatible gold nanoparticles in suspension was found equal to 118 nm, with a polydispersity index (dispersion of the nanoparticles' population in size) of 0.13.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −1 mV.

Example 2

Nanoparticles Prepared with a Conductor Material: Synthesis of Gold Nanoparticles Coated with a Biocompatible Coating Having a Negative Surface Charge Gold nanoparticles were prepared as described in example 1 (same gold inorganic core).

A 0.22 µm filtration on PES membrane filter was performed and gold concentration in suspension was determined by a UV-visible spectroscopy assay at 530 nm.

A biocompatible surface coating was performed using meso-2, 3-dimercaptosuccinic acid (DMSA). A sufficient amount of DMSA was added to the nanoparticles' suspension to reach at least half a monolayer coverage (2.5 molecules/$nm^2$) on the surface. pH was adjusted between 7 and 7.2, and the nanoparticles' suspension was stirred overnight.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The hydrodynamic diameter of the so obtained nanoparticles in suspension was equal to 76 nm, with a polydispersity index (dispersion of the nanoparticles' population in size) of 0.46.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −23 mV.

Example 3

Nanoparticles Prepared with an Insulator Material Having a Low Relative Dielectric Constant Equal to or Below 100: Synthesis of Zirconium Oxide Nanoparticles Coated with a Biocompatible Coating Having a Neutral Surface Charge Zirconium oxide ($ZrO_2$) nanoparticles were synthesized by precipitation of zirconium chloride ($ZrCl_4$) with tetramethyl ammonium hydroxide (TMAOH) at a basic pH. The resulting suspension was transferred in an autoclave and heated at a temperature above 110° C. After cooling, the suspension was washed with deionized water and acidified.

A 0.22 µm filtration on PES membrane filter was performed and ($ZrO_2$) nanoparticles' concentration was determined by drying the aqueous solution into a powder and weighing the as-obtained mass.

A biocompatible coating was prepared using silane-poly (ethylene) glycol 2 kDa ("Si-PEG 2 kDa"). A sufficient amount of "Si-PEG 2 kDa" was added to the nanoparticles' suspension to reach at least half a monolayer coverage (2.5 molecules/$nm^2$) on the surface. The nanoparticles' suspension was stirred overnight and subsequently the pH was adjusted to 7.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 55 nm, with a polydispersity index (dispersion of the nanoparticles' population in size) of 0.1.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH7 was found equal to −1 mV.

Example 4

Nanoparticles Prepared with an Insulator Material Having a Low Relative Dielectric Constant Equal to or Below 100: Synthesis of Zirconium Oxide Nanoparticles Coated with a Biocompatible Coating Having a Negative Surface Charge Zirconium oxide nanoparticles were prepared as described in example 3 (same inorganic core).

A 0.22 μm filtration on PES membrane filter was performed and the ($ZrO_2$) nanoparticles' concentration was determined by drying the aqueous suspension to a powder and weighing the as-obtained mass.

Surface functionalization was performed using sodium hexametaphosphate. A sufficient mass of sodium hexametaphosphate was added to the nanoparticles' suspension to reach at least half a monolayer coverage (2.5 molecules/$nm^2$) on the surface. The nanoparticles' suspension was stirred overnight and pH was subsequently adjusted to 7.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 70 nm, with a polydispersity index (dispersion of the nanoparticles population in size) of 0.11.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH 7 was found equal to −33 mV.

Example 5

Nanoparticles Prepared with a Semiconductor Material: Silicon Nanoparticles Coated with a Biocompatible Coating Having a Negative Surface Charge Silicon (Si) nanoparticles (powder) were obtained from US Research Nanomaterials Inc. They were dispersed in water at 30 g/L under sonication (with a probe).

A 0.22 μm filtration on PES membrane filter was performed and the (Si) nanoparticles' concentration was determined by drying the suspension to a powder and weighing the as-obtained mass.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 164 nm, with a polydispersity index (dispersion of the nanoparticles' population in size) of 0.16.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH7 was found equal to −19 mV.

Example 6

Nanoparticles Prepared with an Insulator Material Having a High Relative Dielectric Constant Equal to or Above 200: Barium Titanate Nanoparticles Coated with a Biocompatible Coating Having a Negative Surface Charge Barium titanate ($BaTiO_3$) nanoparticles' suspension (20% wt in water) was obtained from US Research Materials Inc. (US3835).

Surface functionalization was performed using Silane-poly(ethylene) glycol 10 kDa ("Si-PEG 10 kDa"). Briefly, "Si-PEG 10 kDa" was first dissolved in an ethanol/water solution (1/3 v/v) and added to the $BaTiO_3$ suspension (20% wt in water) to achieve a full monolayer coverage on the surface of the nanoparticles. The suspension was sonicated and subsequently stirred overnight. After a 0.22 μm filtration (filter membrane: poly(ether sulfone)), a washing step was performed in order to eliminate unreacted "Si-PEG 10 kDa" polymers.

The hydrodynamic diameter (measure in intensity) was determined by Dynamic Light Scattering (DLS) with a Nano-Zetasizer (Malvern) at a scattering angle of 173° with a laser emitting at 633 nm, by diluting the nanoparticles' suspension in water (final concentration: 0.1 g/L). The nanoparticles' hydrodynamic diameter was found equal to 164 nm, with a polydispersity index (dispersion of the nanoparticles' population in size) of 0.16.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: 0.1 g/L). The zeta potential at pH7 was found at −11 mV.

Example 7

Evaluation of the Prevention/Rescue Efficacy of Nanoparticles from Examples 1, 2, 5 and 6, Exposed to an Electrical Stimulation on $MPP^+$-Induced Neuronal Networks Using the Phenotypic MEA Screening Technology The prevention/rescue efficacy of nanoparticles of the invention was tested on $MPP^+$-treated mouse ventral midbrain/cortex co-cultures, cultured on a 48-well MEA for 3 weeks. This model represents an in vitro Parkinson's model for screening compounds, based on the functional rescue of dopaminergic neurons using challenged midbrain/cortex cultures growing on MEAs. Midbrain is a region of the brain including the substantia nigra which is part of the basal ganglia and which contains most of the dopaminergic neurons. The evaluation of the nanoparticles' prevention/rescue effect was performed via the measurement of the extracellular electrical activity of the co-culture of neurons plated on MicroElectrode Array (MEA) chips.

The induction of a parkinsonian phenotype in mouse neurons in vitro was performed with 1-methyl-4-phenyl pyridinium iodide (MPP+). There is strong evidence that mitochondrial impairment plays a role in the pathogenesis of Parkinson's disease (PD). MPP was found to be mitochondrial poison that inhibits cellular respiration through the blockade of the electron transport enzyme complex I (NADH: ubiquinone oxidoreductase). Several laboratories have reported that there is a selective defect in complex I of mitochondrial electron transport chain in the substantia nigra of postmortem tissue of PD patients, and there is also reduction of complex I activity in platelets of patients with early PD (Peng J. et al., *Journal of Biomolecular screening,* 2013, 18(5), 522-533: *Using human pluripotent stem cell-derived dopaminergic neurons to evaluate candidate Parkinson's disease therapeutic agents in MPP+ and rotenone models.*).

Material and Methods

Primary Cell Culture, Treatment Conditions and Electrical Stimulation

Midbrain tissue was harvested from embryonic day 14.5 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 µl drop of DMEM containing laminin (10 µg/ml), 10% fetal bovine serum and 10% horse serum on MEAs. Cultures on MEAs were incubated at 37° C. in a 10% $CO_2$ atmosphere until ready for use. Culture media were replenished two times a week with DMEM containing 10% horse serum.

In the "nanoparticles" groups, wells were treated at day 7 with nanoparticles' suspension (800 µM) from examples 1, 2, 5 and with nanoparticles' suspension (2000 µM) from example 6, followed by 20 µM of MPP+ at day 8. In the "control" group, water was added to the wells at day 7, followed by water addition at day 8. In the "MPP+" group, water was added to the wells at day 7, followed by 20 µM of MPP at day 8. Twenty-four (24) hours following MPP (or water for "control" group) addition, the medium was changed to achieve wash out of MPP+. Medium was subsequently changed twice per week.

At day 21, 120 minutes of neuronal activity were recorded, and 30 minutes of stable activity were analyzed. After the recording at day 21, all wells were activated at one of the actively spiking electrodes by electrical stimuli. The stimulation was performed for 30 minutes (stimulation of 1 electrode per well in 48 wells MEA, minimum stimulation duration=100 µs, artefact elimination of 2 ms after pulse, pulse 10×biphasic+/−500 mV). The response of the non-stimulated electrodes was averaged and normalized to pre-stimulation activity (FIG. 6).

Microelectrode Array Neurochips

The 48 wells microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Multichannel Recording and Multiparametric Data Analysis

For the recording, the multichannel MAESTRO recording system by Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$.

Each unit represents the activity originating from one neuron recorded at one electrode. Units are separated at the beginning of the recording. For each unit, action potentials (i.e. spikes), were recorded as spike trains, which are clustered in so-called "bursts". Bursts were quantitatively described via direct spike train analysis using the programs Spike Wrangler and NPWaveX (both NeuroProof GmbH, Rostock, Germany). Bursts were defined by the beginning and end of short spike events (FIG. 7).

With a multiparametric high-content analysis of the network activity patterns, 204 activity-describing spike train parameters were extracted. These parameters allow obtaining a precise description of activity changes in the following four categories: general activity, burst structure, oscillatory behavior and synchronicity.

Changes in "general activity parameters" describe the effects on action potential firing rate (spike rate), burst rate, and burst period as the time between the bursts.

"Burst structure parameters" define not only the internal structure of spikes within a high-frequency spiking phase ("burst"), e.g., spike frequency in bursts, spike rate in bursts, and burst spike density, but also the overall structure of the burst, such as duration, area, and plateau.

"Oscillatory parameters" quantify the regularity of occurrence or structure of bursts, which is calculated by coefficients of variation of primary activity parameters describing the variability of parameters (general activity, burst structure) within experimental episodes (Gramowski A. et al., *Eur. J. Neurosci.,* 2004, 19, 2815-2825: *Substance identification by quantitative characterization of oscillator activity in murine spinal cord networks on microelectrode arrays*). Higher values indicate less regular burst structure or less regular general activity (e.g., spiking, bursting).

As a measure of synchronicity in the spike trains, "CVnet parameters" reflect "synchronization" among neurons within the network (Gramowski A. et al., *Eur. J. Neurosci.,* 2004, 19, 2815-2825: *Substance identification by quantitative characterization of oscillator activity in murine spinal cord networks on microelectrode arrays*). CVnet is the coefficient of variation over the network. Large CVnet values imply a wide range of variation in the activity across the network, meaning less synchronization. (Gramowski A. et al., *Frontiers in Neurology,* 2015, 6(158): *Enhancement of cortical network activity in vitro and promotion of GABAergic neurogenesis by stimulation with an electromagnetic field with* 150 *MHz carrier wave pulsed with an alternating* 10 *and* 16 *Hz modulation*).

Functional effects induced by MPP on neuronal network under electrical stimulation and prevention/rescue efficacy of the nanoparticles of the invention under electrical stimulation were evaluated through the above described parameters (also recapitulated for some of them in the Table 3 below).

TABLE 3

Activity-describing parameters from the multiparametric data analysis in the four following categories: general activity, burst structure, oscillatory behavior and synchronicity.

| | | |
|---|---|---|
| General activity | Spike rate | Number of spikes per second, averaged over all spike trains recorded |
| Burst structure | Burst duration | Mean lengths of bursts (ms), |
| Oscillatory behavior | Burst area CVtime | Coefficient of variation in time of area under the curve after integrating the bursts, defined by burst duration, number of spikes in bursts, spike frequency in bursts. The parameter describes the variability of burst area within experimental episodes. Higher values indicate less regular structure. |
| | Burst peak frequency height CVtime | Coefficient of variation in time of single unit spike peak frequency in bursts. Lower values are a measure indicating more regularity in burst peak frequency, therewith a higher degree of regular burst structure within experimental episodes. |
| | Burst duration CVtime Sum | Coefficient of variation over time of burst duration, reflecting the variability of burst duration within experimental episodes. |
| | Burst period SD Sum | Standard deviation of burst period, reflecting the variation of single unit distances between consecutive bursts within experimental episodes. Lower values reflect higher regularity in burst structure. |
| Synchronicity | Burst rate CVnet | CVnet of burst rate, reflecting variation of burst rate over the network during experimental episodes |
| | Burst period CVnet | CVnet of burst period (distance between the beginning of consecutive bursts) reflecting the variation of "burstiness" within experimental episode over the whole network. Decrease of this parameter reflects an increase in synchronization within the network. |
| | % spikes in burst CVnet | CVnet of percentage of spikes in bursts, reflecting the variation of fraction of spikes within burst intervals of all spikes within experimental episode over the whole network. Decrease of this parameter reflects an increase in synchronization within the network. |
| | SynAll | Average distance of bursts within a population burst from population burst center. SynAll is a measure for the strength of synchronicity of a network. |

MPP$^+$-induced functional effects on network activity under electrical stimulation in the presence or not of the tested nanoparticles were normalized to the "pre-stimulated" activity, i.e. the activity measured at day 21, set at 100% for each experiment. Values related to spontaneous native activity were derived from 60 seconds bin data taken from a 30 minutes span after a 30 minutes stabilization of activity. Results (parameter values) were expressed as mean±SEM of independent networks. For each "nanoparticles" group, at least 8 active wells, for the "control" group, at least 30 active wells and for the "MPP$^+$" group, at least 26 active wells ("active" meaning wells with a sufficient number of electrodes measuring electrical activity), were included in the analysis. The absolute parameters' distributions were tested for normality and the statistical significance between groups was assessed via one-way ANOVA.

FIG. 8 presents some representative parameters from the following categories: oscillatory behavior and synchronicity. These parameters characterize MPP$^+$-induced functional effects under electrical stimulation and the prevention/rescue efficacy allowed by the nanoparticles of the invention under electrical stimulation (i.e. the ability to prevent/rescue functional effects to a level similar to that of "control" group).

To evaluate compound effects, multiparametric results of a selection of 204 parameters were projected into a single parameter termed the "Effect Score". It is a linear combination of selected features, transforming the datasets onto a vector with "control" group exposed to an electric field at a mean value of "0" and "MPP$^+$" group exposed to an electric field at a mean value of "1". Calculation of the Z-factor of the Effect Score was performed through feature selection of 18 out of the 204 parameters measured, optimized to find the best discrimination between the "control" group and the "MPP$^+$" group (Kümmel A, et al. *J Biomol Screen.*, 2010, 15(1), 95-101: *Integration of multiple readouts into the z' factor for assay quality assessment*). The Effect Score analysis is shown in FIG. 9.

The prevention/rescue efficacy of the nanoparticles of the invention exposed to an electrical stimulation is shown in Table 4.

TABLE 4

Summary of Effect Score and prevention/rescue efficacy of nanoparticles of the invention exposed to an electric field, on MPP$^+$-induced effects on neuronal network exposed to an electric field alone.

| Group | Effect Score | Prevention/rescue efficacy | Description of effects |
|---|---|---|---|
| "control" group | 0 | Reference (set at 100%) | — |
| "MPP$^+$" group | 1 | 0% | — |
| "nanoparticles" group: biocompatible gold nanoparticles from example 1 | 0.43 | 56% | Prevention of ⅔ of MPP+ effects |
| "nanoparticles" group: biocompatible gold nanoparticles from example 2 | 0.72 | 28% | Prevention of ⅓ of MPP+ effects |
| "nanoparticles" group: biocompatible silicon nanoparticles from example 5 | 0.65 | 35% | Prevention of ⅓ of MPP+ effects |

TABLE 4-continued

Summary of Effect Score and prevention/rescue efficacy of nanoparticles of the invention exposed to an electric field, on MPP+-induced effects on neuronal network exposed to an electric field alone.

| Group | Effect Score | Prevention/rescue efficacy | Description of effects |
|---|---|---|---|
| "nanoparticles" group: biocompatible barium titanate nanoparticles from example 6 | 0.64 | 36% | Prevention of ⅓ of MPP+ effects |

The treatment of Parkinson's disease symptoms by DBS is FDA-approved since 2002. The most commonly used stimulatory parameters, usable in the context of the invention in combination with the herein described nanoparticles are: 130 to 185 Hz in frequency, 60 to 210 µs in pulse width and 1 to 3.5 V in voltage amplitude. In the herein described experimentations, the stimulation was performed on the neuron network co-culture for 30 minutes, with stimulus=10 biphasic pulses (pulse duration=100 µs), pulse amplitude=+/−500 mV, pulse frequency=20 Hz, and a pulse trains period=0.2 Hz.

FIGS. 12, 13 and Table 4 show that pretreatment of the neuronal network with nanoparticles of the invention and exposition to an electric field, prevents/rescues MPP induced functional effects under electric field on the neuronal network. Interestingly, the prevention/rescue efficacy is observed for parameters in categories related to oscillatory behavior and synchronicity, and it can reach a level up to what is observed in "control" group. These oscillatory behavior and synchronization parameters are typically monitored as a measure of altered network development. These parameters can advantageously be rescued in presence of the nanoparticles of the invention exposed to an electrical stimulation.

These results highlight the advantageous performances of the nanoparticles described in the present application, when exposed to an electric field, in rescuing MPP+-induced functional effects under electric field on the neuronal network.

Example 8

Evaluation of the Effects of the Nanoparticles from Examples 2, 3, 4 and 5 Exposed to an Electrical Stimulation on Amyloid Beta 1-42-Induced Functional Effects on Primary Mouse Neuronal Networks Using the Phenotypic MEA Screening Technology The rescue efficacy of nanoparticles of the invention exposed to an electrical stimulation was tested in vitro via MEAs on an amyloid beta 1-42 (Abeta 1-42)-induced model of Alzheimer's disease in frontal cortex cultures of mouse neurons.

To induce an Alzheimer-related functional phenotype, synthetic HFIP (hexafluoroisopropanol)-treated Abeta 1-42 peptides (HFIP treatment produces monomers of amyloid beta) are used at a sub-toxic dose (100 nM). High levels of amyloid-beta (Abeta) reduce glutamatergic synaptic transmission and cause synaptic loss (Palop et al., Nat Neurosci., 2010, 13(7), 812-818: Amyloid-beta induced neuronal dysfunction in Alzheimer's disease: from synapses toward neural networks; Hsia et al., Proc. Natl. Acad. Sci., 1999, 96, 3228-3233: Plaque-independent disruption of neural circuits in Alzheimer's disease mouse models). The production of Abeta and its secretion into the extracellular space are tightly regulated by neuronal activity in vitro and in vivo. Increased neuronal activity enhances Abeta production, and blocking neuronal activity has the opposite effect. This synaptic regulation of Abeta is mediated, at least in part, by clathrin-dependent endocytosis of surface amyloid precursor protein (APP) at presynaptic terminals, endosomal proteolytic cleavage of APP, and Abeta release at synaptic terminals (Cirrito et al., Neuron, 2005, 48, 913-922: Synaptic activity regulates interstitial fluid amyloid-beta levels in vivo).

Material and Methods

Primary Cell Culture

Frontal cortex tissue was harvested from embryonic day 15/16 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 µl drop of DMEM containing laminin (10 µg/ml), 10% fetal bovine serum and 10% horse serum on MEAs. Cultures on MEAs were incubated at 37° C. in a 10% $CO_2$ atmosphere until ready for use. Culture media were replenished two times a week with DMEM containing 10% horse serum. The developing co-cultures were treated with the mitosis inhibitors 5-fluoro-2'-deoxyuridine (25 µM) and uridine (63 µM) on day 5 after seeding to prevent further glial proliferation.

In the "nanoparticles" groups, wells were first treated with Abeta 1-42 (synthetic HFIP-treated Amyloid-beta 1-42 peptides) at T0 (T0 being at the end of the 28 days-in vitro culture period). Wells were then treated at T0+4 hours with the nanoparticles' suspension from examples 2, 3, 4 and 5 (each suspension being at a concentration of 800 µM) in independent and parallel experiments. In the "Control" group, water was added to the wells at T0, and then at T0+4 hours. In the "Abeta" group, Abeta 1-42 was added to the wells at T0, and then water was added to the wells at T0+4 hours.

Neuronal activity was recorded as follows:
At T0, prior Abeta 1-42 addition (or water in the "control" group)
At T0+1 h, T0+2 h, T0+3 h, T0+4 h (prior addition of the nanoparticles in the «nanoparticles» group or "water" in the control group), T0+5 h and T0+6 h.

Values were derived from 60 seconds bin data taken from a 30 minutes span after a 30 minutes stabilization of activity.

After the recording at T0+6 h, all wells were activated at one of the actively spiking electrode by electrical stimuli. The stimulation was performed for 30 minutes (stimulation of 1 electrode per well in 48 wells MEA, minimum stimulation duration=100 µs, artefact elimination of 2 ms after pulse, pulse 10×biphasic+/−500 mV). The response of the non-stimulated electrodes was averaged and normalized to pre-stimulation activity (FIG. 10).

Microelectrode Array Neurochips

The 48 wells microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Multichannel Recording and Multiparametric Data Analysis

For the recording, the multichannel MAESTRO recording system from Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$. The action potentials, or "spikes", were recorded in spike trains and were clustered in so-called "bursts". Bursts were quantitatively described via direct spike train analysis using the programs Spike Wrangler and NPWaveX (both Neuro-Proof GmbH, Rostock, Germany). Bursts were defined by the beginning and end of short spike events.

With a multiparametric high-content analysis of the network activity patterns, 204 activity-describing spike train parameters were extracted. These parameters allow obtaining a precise description of activity changes in the four categories as follows: general activity, burst structure, oscillatory behavior and synchronicity.

Functional effects of amyloid beta 1-42 on neuronal network exposed to electrical stimulation and rescue efficacy of functional effects of the neuronal network by the nanoparticles of the invention exposed to an electrical stimulation were evaluated through the above described parameters (also recapitulated for some of them in Table 5 below).

TABLE 5

Activity-describing parameters from the multiparametric data analysis in the four following categories: general activity, burst structure, oscillatory behavior and synchronicity

| | | |
|---|---|---|
| General activity | Spike contrast | Describes the occurrence or absence of spikes in neighboring time segments of the spike train, reflecting the variability in burstiness of units within experimental episodes |
| Burst structure | Burst duration sum | Mean lengths of burst (ms) |
| Oscillatory behavior | Burst rate SD | Standard deviation of number of bursts per minute, indicating the variability of burstiness of units within experimental episodes |
| | Burst period SD | Standard deviation of burst period, reflecting the variation of single unit distances between consecutive bursts within experimental episodes. Low values reflect higher regularity in the burst structure |
| Synchronicity | Burst spike rate CVnet | CVnet of burst spike rate, reflecting the variation of spikes within burst intervals within experimental episodes over the whole network. Decrease of this parameter reflects an increase in synchronization within the network |
| | Spike contrast CVnet | CVnet of spike contrast. Higher values indicate higher variability of "burstiness" of units among the network |

Network activity under stimulation was normalized to the related spontaneous native activity (T0+6 hours recording), set at 100% for each experiment. Values related to spontaneous native activity were derived from 60 seconds bin data taken from a 30 minutes span after a 30 min stabilization of activity. Results (parameter values) were expressed as mean±SEM of independent networks. For each "nanoparticles" group, at least 9 active wells, for the "control" group, at least 18 active wells, and for the "Abeta" group, at least 18 active wells ("active" meaning wells with a sufficient number of electrodes measuring electrical activity), were included in the analysis. The absolute parameters' distributions were tested for normality and the statistical significance between groups was assessed via one-way ANOVA.

FIG. 11 shows some representative parameters from the following categories: general activity, burst structure, oscillatory behavior and synchronicity.

These parameters characterize Abeta 1-42-induced functional effects under electrical stimulation and the rescue efficacy allowed by the nanoparticles of the invention under electrical stimulation (i.e. the ability to prevent/rescue functional effects to a level similar to that of "control" group).

To evaluate compound effects, multiparametric results of a selection of 204 parameters were projected into a single parameter termed the "Effect Score". It is a linear combination of selected features, transforming the datasets onto a vector with "control" group exposed to an electric field at a mean value of "0" and "Abeta" group exposed to an electric field at a mean value of "1". Calculation of the Z-factor of the Effect Score was performed through features' selection of 15 out of the 204 parameters measured, optimized to find the best discrimination between the "control" group and the "Abeta" group (Kümmel A, et al., *J Biomol Screen.*, 2010, 15(1), 95-10: *Integration of multiple readouts into the z' factor for assay quality assessment*). The Effect Score analysis is shown in FIG. 12.

The rescue efficacy of the nanoparticles of the invention exposed to an electrical stimulation is shown in Table 6.

TABLE 6

Summary of Effect Score and rescue efficacy of the nanoparticles of the invention exposed to an electric field on Abeta 1-42-induced effects on the neuronal network exposed to an electric field alone.

| Group | Effect Score | Rescue efficacy | Description of effects |
|---|---|---|---|
| "control" group | 0 | Reference (set at 100%) | — |
| "Abeta" group | 1 | 0% | — |
| "nanoparticles" group: biocompatible gold nanoparticles from example 2 | 0.43 | 25% | Prevention of ¼ of Abeta 1-42 effects |
| "nanoparticles" group: biocompatible zirconium oxide nanoparticles from example 3 | 0.72 | 45% | Prevention of ½ of Abeta 1-42 effects |
| "nanoparticles" group: biocompatible zirconium oxide nanoparticles from example 4 | 0.65 | 34% | Prevention of ⅓ of Abeta 1-42 effects |
| "nanoparticles" group: biocompatible silicon nanoparticles from example 5 | 0.64 | 34% | Prevention of ⅓ of Abeta 1-42 effects |

Clinical investigations are ongoing to evaluate the potential of DBS for the treatment of Alzheimer's disease. The stimulatory parameters, typically usable in the context of the invention in combination with the herein described nanoparticles, are: 130 Hz in frequency, 60 or 90 µs in pulse width, 3 to 5 V in amplitude voltage. In the herein described experimentations, the stimulation was performed on the neuron network coculture for 30 minutes, with stimulus=10 biphasic pulses, with minimum pulse duration=100 µs, pulse amplitude=+/−500 mV, pulse frequency=20 Hz, and a pulse trains period=0.2 Hz.

FIGS. 11 and 12 and Table 6 show that treatment of the neuronal network with nanoparticles of the invention, when exposed to an electric field, rescues Abeta 1-42 induced functional effects under electric field of the neuronal network. Interestingly, the rescue efficacy is observed for parameters in categories related to oscillatory behavior and synchronicity and it can reach a level up to what is observed in the "control" group.

These oscillatory behavior and synchronization parameter are typically monitored as a measure of altered network development. These parameters can advantageously be rescued in presence of the nanoparticles of the invention exposed to an electrical stimulation.

These results highlight the advantageous performances of the nanoparticles described in the present application, when exposed to an electric field, in rescuing Abeta 1-42 induced functional effects under electric field on the neuronal network.

The invention claimed is:

1. A method for treating a neurological disease or at least one symptom thereof in a subject, wherein the method comprises i) administering a nanoparticle or nanoparticle aggregate to the subject, the nanoparticle or nanoparticle aggregate material being selected from a conductor material selected from a metal having a standard reduction potential E° above 0.2 selected from Tl, Po, and Ir, or an organic material having contiguous sp2 hybridized carbon centers in its structure selected from a polyaniline, polypyrrole, polyacetylene, polythiophene, polycarbazole and/or polypyrene, a semiconductor material with a band gap Eg below 3.0 eV, selected from an element from group IVA of the Mendeleev periodic table that is doped with a charge carrier selected from Al, B, Ga, In and P, an insulator material with a band gap Eg equal to or above 3.0 eV and with a dielectric constant $\varepsilon_{ijk}$ equal to or above 200 which is a mixed-metal oxide selected from $BaTiO_3$, $KTaNbO_3$ $KTaO_3$ $SrTiO_3$ and $BaSrTiO_3$, and an insulator material with a band gap Eg equal to or above 3.0 eV and with a dielectric constant $\varepsilon_{ijk}$ equal to or below 100 selected from $LaAlO_3$, $La_2O_3$, $CeO_2$, $SiO_2$, $SnO_2$, $Ta_2O_5$, $ZrO_2$, $HfO_2$, and ii) exposing the nanoparticle or nanoparticle aggregate to an electric field, wherein the subject's abnormal neuronal network oscillatory behavior and/or synchronicity is at least partially rescued by the treatment.

2. The method according to claim 1, wherein the electric field is applied through deep brain stimulation, transcranial electric stimulation or transcranial magnetic stimulation.

3. The method according to claim 1, wherein the relative dielectric constant $\varepsilon_{ijk}$ is measured between 20° C. and 30° C. and between $10^2$ Hz up to the infrared frequency.

4. The method according to claim 1, wherein the neurological disease is selected from Parkinson disease, Alzheimer disease, epilepsy, obsessive compulsive disorder, autism spectrum disorder, depression disorder, dystonia, Tourette syndrome, schizophrenia, stroke, aphasia, dementia, tinnitus, Huntington disease, essential tremor, bipolar disorder, anxiety disorder, addiction disorder, consciousness vegetative state, and at least one symptom thereof.

5. A method for treating a neurological disease or at least one symptom thereof in a subject, wherein the method comprises i) administering a composition to the subject, the composition comprising nanoparticles and/or nanoparticle aggregates and a pharmaceutically acceptable support, and the nanoparticle or nanoparticle aggregate material being selected from a conductor material selected from a metal having a standard reduction potential E° above 0.2 selected from Tl, Po, and Ir, or an organic material having contiguous sp2 hybridized carbon centers in its structure selected from a polyaniline, polypyrrole, polyacetylene, polythiophene, polycarbazole and/or polypyrene, a semiconductor material with a band gap Eg below 3.0 eV, selected from an element from group IVA of the Mendeleev periodic table that is doped with a charge carrier selected from Al, B, Ga, In and P, an insulator material with a band gap Eg equal to or above 3.0 eV and with a dielectric constant $\varepsilon_{ijk}$ equal to or above 200 which is a mixed-metal oxide selected from $BaTiO_3$, $KTaNbO_3$ $KTaO_3$ $SrTiO_3$ and $BaSrTiO_3$, and an insulator material with a dielectric constant $\varepsilon_{ijk}$ equal to or below 100 with a band gap Eg equal to or above 3.0 eV and selected from $LaAlO_3$, $La_2O_3$ $CeO_2$ $SiO_2$ $SnO_2$, $Ta_2O_5$, $ZrO_2$ $HfO_2$, and ii) exposing the subject to an electric field, wherein the subject's abnormal neuronal network oscillatory behavior and/or synchronicity is at least partially rescued by the treatment.

6. The method according to claim 5, wherein the composition comprises at least two distinct nanoparticles and/or nanoparticle aggregates.

7. A kit comprising at least two distinct nanoparticles and/or nanoparticle aggregates, each nanoparticle or nanoparticle aggregate comprising a distinct material selected from a conductor material selected from a metal having a standard reduction potential E° above 0.2 selected from Tl, Po, and Ir, or an organic material having contiguous sp2 hybridized carbon centers in its structure selected from a polyaniline, polypyrrole, polyacetylene, polythiophene, polycarbazole and/or polypyrene, a semiconductor material with a band gap Eg below 3.0 eV, selected from an element from group IVA of the Mendeleev periodic table that is doped with a charge carrier selected from Al, B, Ga, In and P, an insulator material with a band gap Eg equal to or above 3.0 eV and with a dielectric constant $\varepsilon_{ijk}$ equal to or above 200 which is a mixed-metal oxide selected from $BaTiO_3$, $KTaNbO_3$ $KTaO_3$ $SrTiO_3$ and $BaSrTiO_3$ and an insulator material with a dielectric constant $\varepsilon_{ijk}$ equal to or below 100 with a band gap Eg equal to or above 3.0 eV and selected from $LaAlO_3$, $La_2O_3$ $CeO_2$ $SiO_2$ $SnO_2$ $Ta_2O_5$ $ZrO_2$ $HfO_2$, wherein the subject's abnormal neuronal network oscillatory behavior and/or synchronicity is at least partially rescued by the treatment.

8. The kit according to claim 7 for treating a neurological disease or at least one symptom thereof in a subject.

9. The method according to claim 1, wherein the treatment of said neurological disease or at least one symptom thereof in the subject is caused by the step of exposing the nanoparticle or nanoparticle aggregate to the electric field.

* * * * *

UNITED STATES PATENT AND TRADEMARK OFFICE
CERTIFICATE OF CORRECTION

PATENT NO. : 11,278,723 B2
APPLICATION NO. : 16/472214
DATED : March 22, 2022
INVENTOR(S) : Marie-Edith Meyre et al.

Page 1 of 1

It is certified that error appears in the above-identified patent and that said Letters Patent is hereby corrected as shown below:

In the Specification

<u>Column 31,</u>
Line 3, "MPP was" should read --$MPP^+$ was--.
Line 39, "MPP at" should read --$MPP^+$ at--.
Line 39, "following MPP" should read --following $MPP^+$--.

<u>Column 32,</u>
Line 62, "MPP" should read --$MPP^+$--.

<u>Column 35,</u>
Line 25, "MPP" should read --$MPP^+$--.

Signed and Sealed this
Twenty-fourth Day of January, 2023

Katherine Kelly Vidal
*Director of the United States Patent and Trademark Office*